US011464589B1

(12) United States Patent
Roh et al.

(10) Patent No.: US 11,464,589 B1
(45) Date of Patent: Oct. 11, 2022

(54) ROBOTIC SYSTEM AND METHOD FOR PERFORMING LATENCY MANAGED TELESURGERY

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/685,221

(22) Filed: Mar. 2, 2022

(51) Int. Cl.
| A61B 34/00 | (2016.01) |
| A61B 34/35 | (2016.01) |
| G16H 40/20 | (2018.01) |
| G16H 40/67 | (2018.01) |
| G05D 1/00 | (2006.01) |
| A61B 17/00 | (2006.01) |

(52) U.S. Cl.
CPC ............ *A61B 34/35* (2016.02); *G05D 1/0027* (2013.01); *G16H 40/20* (2018.01); *G16H 40/67* (2018.01); *A61B 2017/00477* (2013.01)

(58) Field of Classification Search
CPC .......... A61B 34/35; A61B 2017/00477; G05D 1/0027; G16H 40/20; G16H 40/67
See application file for complete search history.

(56) References Cited

U.S. PATENT DOCUMENTS

| 11,389,064 | B2 * | 7/2022 | Sanchez | ................ | G16H 40/67 |
| 11,395,703 | B2 * | 7/2022 | Berman | ................ | A61B 34/30 |
| 11,399,153 | B2 * | 7/2022 | Temby | ................ | H04N 7/142 |
| 2022/0226062 | A1 * | 7/2022 | Pflaumer | ................ | A61B 34/30 |

* cited by examiner

*Primary Examiner* — Masud Ahmed
(74) *Attorney, Agent, or Firm* — Perkins Coie LLP

(57) ABSTRACT

Robotic system and method are described for performing latency managed telesurgery. The system comprises drone(s) to create a wireless network in one or more geographic areas between a surgical site and a remote surgeon. The system further comprises a computer that is configured to: receive a request that indicates that a telesurgery is to be performed between the first location and the second location at a scheduled time; determine that one or more equipment is available for use at the surgical site for the telesurgery at the scheduled time; send a first instruction that triggers measurement of a latency of the wireless network; determine, during the telesurgery, whether the latency of the wireless network is acceptable; and send a first message that indicates that the latency is not acceptable, where an operation of the drone(s) is adjusted or an additional drone is deployed in the one or more geographic areas.

20 Claims, 20 Drawing Sheets

| MEDICAL DATABASE |||||||
|---|---|---|---|---|---|---|
| PATIENT DATA ||||||
| NAME | AGE | WEIGHT | DIAGNOSIS | IMAGES | FAMILY MEDICAL HISTORY |
| ALEX | 34 | 74 | LEG FRACTURE | IMAGE 1 | HIGH BLOOD PRESSURE TO MOTHER |
| | | | | IMAGE 2 | DIABETES TO FATHER |
| | | | | IMAGE 3 | GRANDFATHER DIED OF KIDNEY CANCER |

| SURGERY DATA ||||||
|---|---|---|---|---|---|
| NAME | REAL-TIME IMAGING DATA | PRE-PLAN FOR SURGERY | TYPE OF SURGERY | SURGICAL SITE | EXPECTED OUTCOME |
| ALEX | IMAGE OF LEFT LEG | MEDICATION FOR NUMBING THE LEFT LEG | SURGICAL OPERATION FOR FRACTURE | LOWER PORTION OF LEFT LEG | STABLE LEFT LEG WITH NO PAIN AND NO SIDE EFFECTS (INCLUDING NORMAL BLOOD PRESSURE) |
| | MRI SCAN | | | | |
| | X-RAY IMAGE OF LEFT LEG | | | | |

*FIG. 7*

ROBOTIC SYSTEM AND METHOD FOR PERFORMING LATENCY MANAGED TELESURGERY

TECHNICAL FIELD

The present disclosure is generally related to systems and methods for performing telesurgery, and more particularly related to systems for performing low latency telesurgery.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 illustrates a medical database for the system, according to an embodiment.

DETAILED DESCRIPTION

Figure 1:
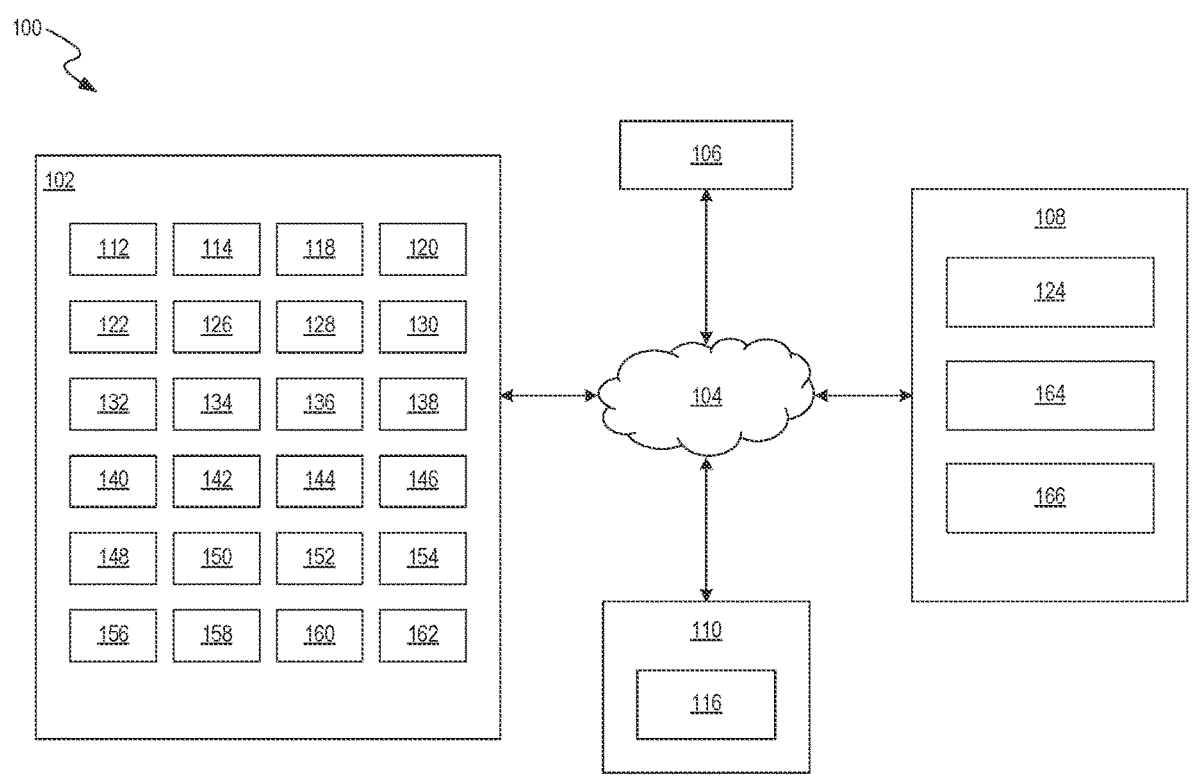
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples.

Throughout this specification, plural instances (e.g., "602") may implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

Developments in telesurgery has enabled a physician to operate on a patient who may not be in the same location as the physician. However, for a telesurgery to be successful, a network between the physician's location and the patent's location needs to perform well. However, there may be several scenarios in which a network may not perform well for telesurgery. For example, a network between the physician's location and the patient's location may be located in one or more geographical areas where the presence of communication infrastructure (e.g., cell towers, underground communication cables, etc.) is well established but the network may have a high latency due to congestion. In other example, a network may not be present in remote parts of the world or if present in some parts of the world, may have a high latency. In some cases, due to respiration of the patient, latency can become a major health and safety issue for remote surgery. In this patent document, the term latency can be used interchangeably with the term bandwidth. Bandwidth can, for example, determine the resolution, quality, and continuity of data that can be provided to a remote surgeon. In some embodiments, both Latency and bandwidth can be important.

To address at least these technical problems with latency, this patent document describes systems, methods, and apparatus that can be used for a latency managed telesurgery. A system can manage drones to provide a network supporting a telesurgery procedure. An example system may include at least two computers. A first computer that can be used to deploy one or more drones in one or more geographic areas between the physician's location and the patient's location so that the one or more drones can create or be a part of a network. A second computer can at least determine whether a latency of the network is acceptable during the telesurgery. If the second computer determines that the latency is not acceptable, then the second computer can send a message to the first computer that can trigger the first computer to adjust the operation of the one or more drones (e.g., move at least one drone) or deploy one or more additional drones. In this patent document, the term "drone" may include an unmanned vehicle, an unmanned craft, an unmanned aircraft, a ground or aerial vehicle, an aerospace craft, a satellite orbiting the earth (e.g., a geosynchronous satellite or a satellite in an array of low earth orbit satellites). For example, drones can be fixed wing drones, single rotor drones, tilt-wing drones, or multirotor drones. A networked group of drones can include different types of drones. In one implementation, a networked group can include, for example, fixed wing drones for long flight times, single rotor drones for carrying heavy communication equipment, and multirotor drones for hovering at specified locations. The number and configuration of drones can be selected based on the communication capabilities of the network.

This patent document first introduces robotic surgery in Section I and then describes systems, methods, and apparatus to perform latency managed telesurgery in Section II. In Section III, this patent document describes techniques and/or devices to manage data connections, manage latency, support telesurgery assistance, and/or perform telesurgery. The example headings for the various sections below are used to facilitate the understanding of the disclosed subject matter and do not limit the scope of the claimed subject matter in any way. Accordingly, one or more features of one example section can be combined with one or more features of another example section.

I. Introduction to Robotic Surgery

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgery technologies disclosed offer valuable enhancements to medical or surgical processes through improved precision, stability, and dexterity. The disclosed methods relieve medical personnel from routine tasks and make medical procedures safer and less costly for patients. The embodiments disclosed enable performing more accurate surgery in more minute locations on or within the human body. The embodiments also and address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgically performed procedures according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center. In some embodiments, the operating room 102 is a mobile surgical room, battlefield surgical room, surgical site at a remote location, etc. and can be in communication with the console 108 via the network 104. As further described in this patent document, networked drones can be used to provide the network 104 capable of supporting any number of telesurgery procedures. In some embodiments, the console 108 can be located in the operating room 102.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or $SpO_2$ monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of a target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end-effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body.

An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors comprise a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of tool—tissue interaction forces. During MIS, the field of view and workspace of tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"— of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for the fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a postoperative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table which is designed for use in spinal surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskobo-inikova apparatus. A corrective tool refers to a tool designed to gradually correct a deformity, e.g., corsets, splints, orthopedic footwear, insoles, and other devices to correct abnormal positions of the foot. A compression-distraction tool refers to a tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can comprise a physical drill, power cord, electronically motorized bone drill, or rotating bone shearing incision work unit.

In some embodiments, the tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can comprise a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment 102. The consumables 158 can include gloves, gowns, masks, syringes, needles, sutures, staples, tubing, catheters, or adhesives for wound dressing, in addition to other tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
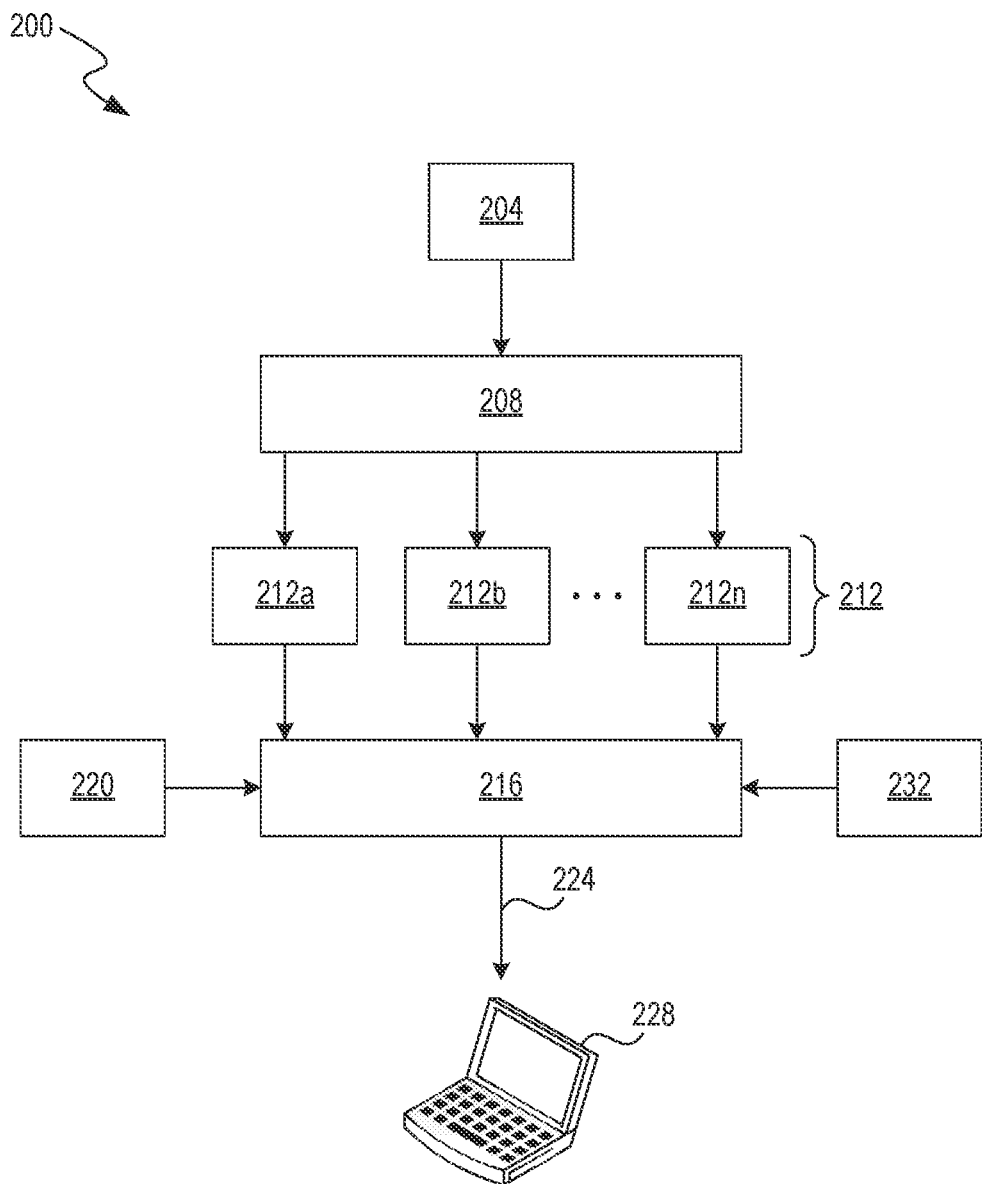
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, sem idefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
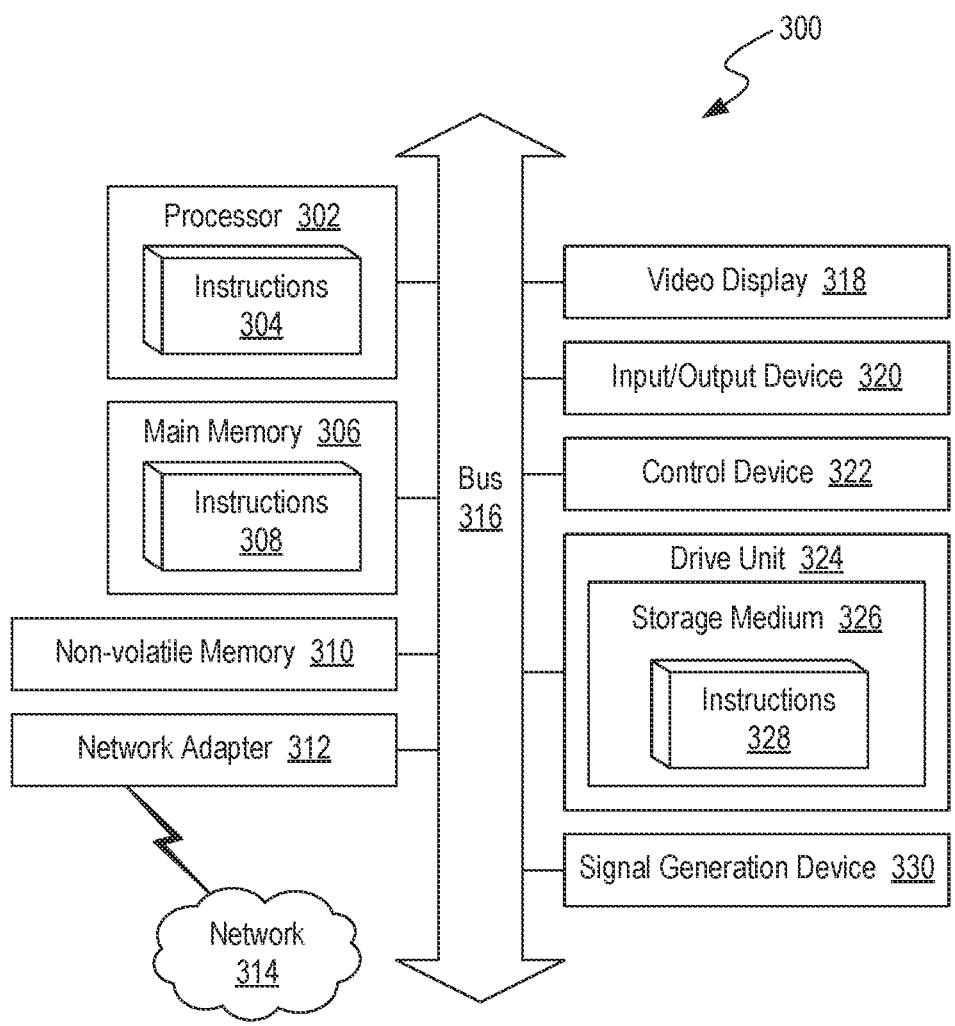
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
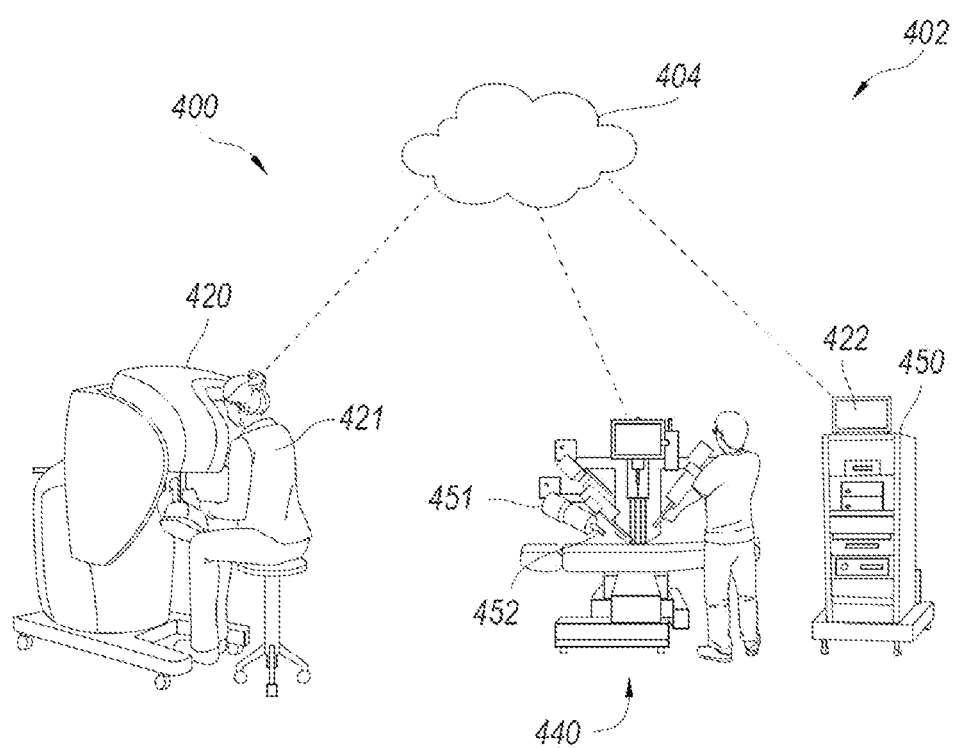
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and may include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include preoperative images, such as MRI, CT, PET, etc. The various imaging modalities can be selectable, programmed, superimposed and/or can include other information superimposed in graphical and/or numerical or symbolic form.

The robotic surgical system 400 can include multiple consoles 420 to allow multiple users to simultaneously or sequentially perform portions of a surgical procedure. The number and configuration of consoles 420 can be selected based on the surgical procedure to be performed, number and configurations of surgical robots, surgical team capabilities, or the like.

Figure 4B:
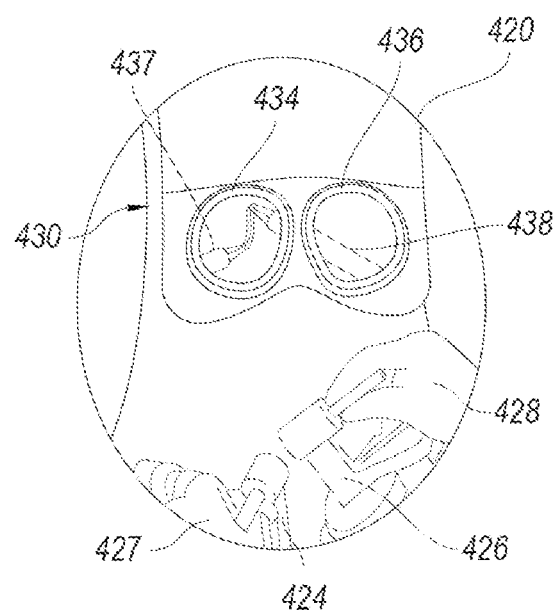
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. A trigger can be implemented in software to execute a jump to a particular instruction or step of a program. A trigger can be implemented in hardware, e.g., by applying a pulse to a trigger circuit. Different example modes are discussed below.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure.

Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring.

In some embodiments, the robotic surgical system 400 can determine whether a detected event is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre- or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems may be used with many different systems for conducting robotic or minimally invasive surgery. One example of a surgical system and surgical robots which may incorporate methods and technology is the DAVINCI™ system available from Intuitive Surgical, Inc.™ of Mountain View, Calif. However, other surgical systems, robots, and apparatuses may be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Simulations for a virtual robotic surgical procedure can be performed using virtual models that can include two or three-dimensional models to evaluate, for example, one or more steps of a surgical procedure (or entire procedure), predicted events, outcomes, etc. The simulations can be used to identify and assess access paths, stresses, strains, deformation characteristics (e.g., load deformation characteristics, load distributions, etc.), fracture characteristics (e.g., fracture toughness), fatigue life, etc. The virtual model can include a model of the patient's anatomy, implant(s), end effectors, instruments, access tools, or the like. The one or more processors can generate a three-dimensional mesh to analyze models. Machine learning techniques to create an optimized mesh based on a dataset of anatomical features and implants or other devices. The three-dimensional models, surfaces, and virtual representations can be generated by computer-aided design (CAD) software, finite element analysis (FEA) software, and robotic control software/programs based on patient data (e.g., images, scans, etc.), implant design data, or the like. A user can view, manipulate (e.g., rotate, move, etc.), modify, set parameters (e.g., boundary conditions, properties, etc.) and interact with the models. The control parameters, robotic kinematics, and functionality can be used to generate the simulations. In some embodiments, models of end effectors of a robotic system and generated to perform virtual procedures on virtual anatomical models. Virtual simulations of surgical procedures in which a user selected robotic surgical steps and physician steps can be used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques. The healthcare provider can select the surgical robot configuration and surgical plan based, at least in part, on the simulations. End effectors and tools of the surgical robot, imaging equipment, and manual equipment can be selected based on the simulations.

Figure 6:
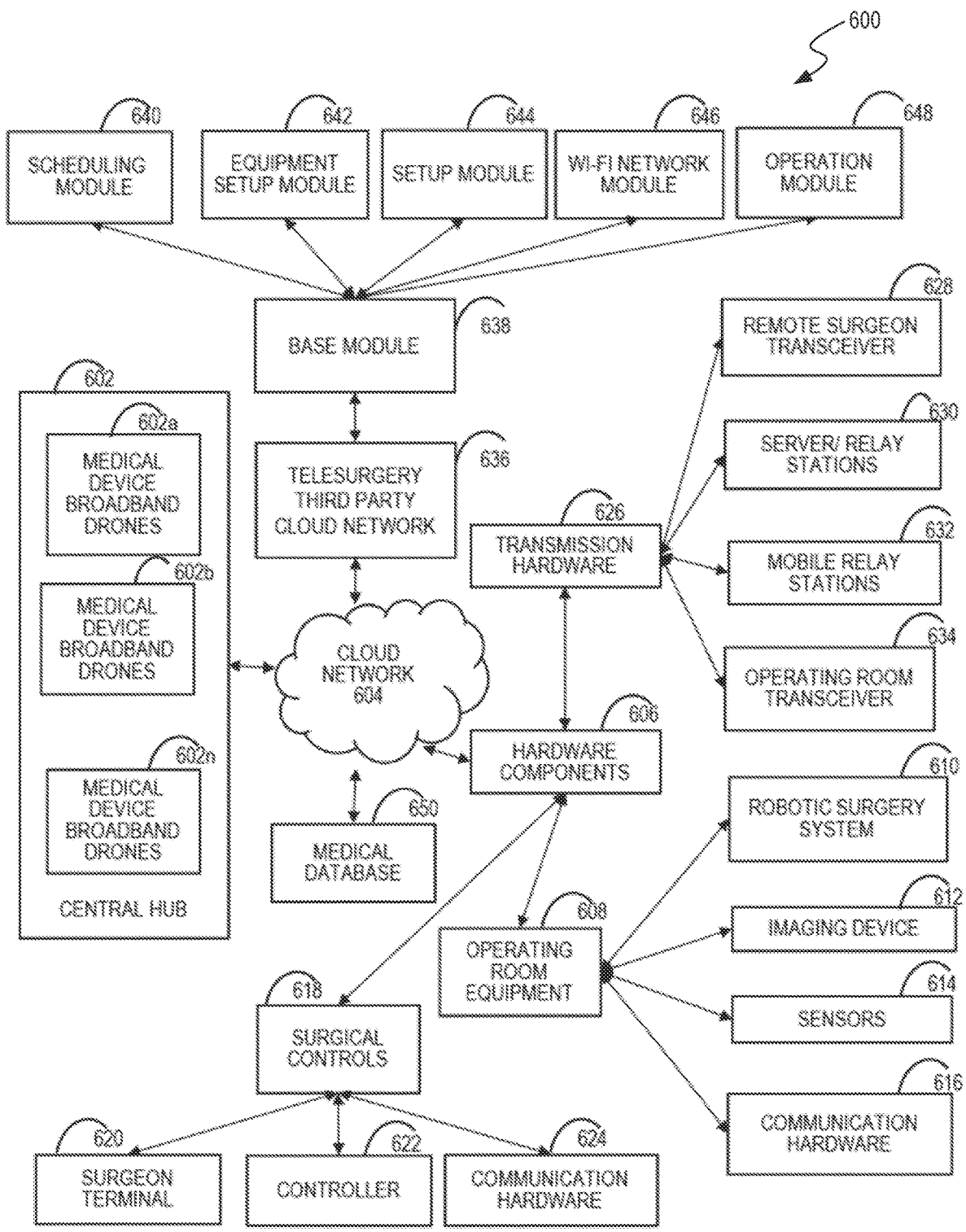
FIG. 6 illustrates a block diagram of a system for performing low latency telesurgery, according to an embodiment.

In some embodiments, the surgical system of FIG. 6 performs virtual simulations based on one more design parameters, including simulation time, resource usage, accuracy level, and/or data output. The simulation time can be selected so that the virtual simulation is completed within a time period (e.g., percentage of completion time for a surgical step, percentage of surgical procedure duration, user-input time period, etc.). The complexity of the models can be increased or decreased to decrease or increase, respectively, the simulation time period. If the user requests a significant amount of data output (e.g., loads applied to anatomical structures, multiple implants, fatigue life, etc.), high complexity models (e.g., FEA models with a large number of elements/nodes, optimization models, fluid flow models, etc.) can be generated. Resource usage parameters can be used to select features of three-dimensional models of the anatomy and implants based on available processing resources, including central processing unit (CPU) cycles, memory space, network bandwidth, or a combination thereof. For example, the resource usage parameters can be set to limit usage of such processing resource(s). The surgical system can perform one or more corrective measures to free up the amount of required resources to enable process resources to be available to the robotic apparatus to complete tasks. The corrective measures can include one or more of allocating memory space, prioritizing packets, limiting CPU usage, and/or throttling bandwidth (e.g., throttling network bandwidth). The complexity and features (e.g., surface contours, feature matching, etc.) can be selected based on the available computing resources.

The surgical system can determine the simulation time period based on an action schedule of the surgical plan, a time allocated for the least one robotic surgical action to be planned and completed, etc. The virtual simulations can be performed while one or more instruments are at least partially positioned within a patient to complete a current surgical action. This allows simulations to be performed concurrently with surgical actions on the patient. Bronchoscopes, endoscopes, and/or imaging equipment are at least partially positioned within the patient to obtain the intraoperative patient data.

Virtual surgical procedures can include one or more robotic assisted surgical steps, automated surgical steps, and/or physician-controlled surgical steps. Intraoperative virtual simulations can be performed at any time during a surgical procedure to plan future surgical steps or actions. The system can collect real-time surgical data, patient data, other information continuously or periodically before, after, and/or during surgical steps. Surgical plans can be modified based on intraoperative planning, trained learning machine models, virtual simulations, etc., and obtained data, such as pre-operative data, intra-operative data (e.g., surgical robot data, patient data, etc.), and/or other data. In some embodiments, virtual simulations are performed based on intraoperative patient data. The virtual simulations can be used to generate one or more robotic surgical actions for an intra-operative surgical plan, drone control plans, latency settings, etc., using a trained machine learning model 216 (see FIG. 2). For example, the surgical system can control a robotic surgical apparatus (e.g., the surgical robot 440 of FIGS. 4A-4B) to perform the robotic surgical action according to the intra-operative surgical plan. Planned robotic surgical actions can be generated any number of times to dynamically modify the intra-operative surgical plan. The real-time planning enables one or more trained machine learning models to determine surgical steps based on the current status of the patient, functionality of the surgical robotic apparatus, etc. If the surgical robotic apparatus is not configured for performing surgical action(s), a user can be notified that the configuration of the surgical robotic apparatus should be modified by, for example, changing end effectors, installing new instruments, etc. Once reconfigured, the surgical robotic apparatus can continue in autonomous mode, semi-autonomous mode, or another mode.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

The virtual simulations can be also used to generate drone control plans for managing networks for the surgical plans. Planned network actions (e.g., repositioning of drones, addition/removal of drones, etc.) can be generated any number of times to dynamically modify the drone control plans. Real-time planning enables one or more trained machine learning models to determine network management steps based on the current status of data transfer, latency, the patient, functionality of surgical robotic apparatus, etc. Drone control plans can be generated based on available resources scheduled by the pre-operative plans. If a resource (e.g., drone, transmission tower, etc.) becomes unavailable, the drone control plan can be adjusted for the change in resources. A user can be alerted if additional resources are recommended.

Figure 5:
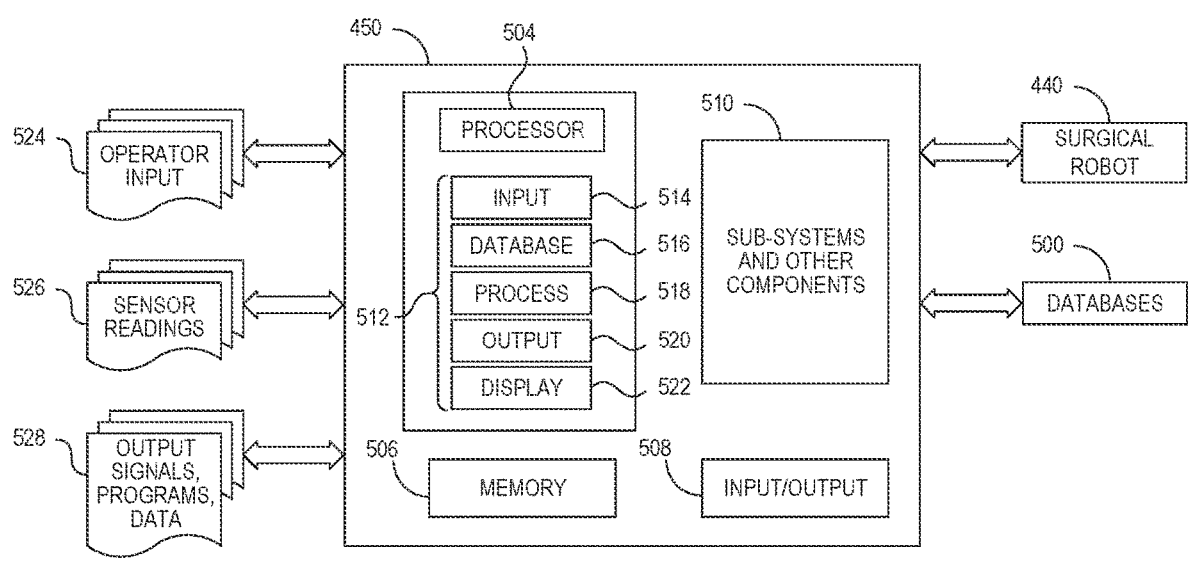
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 may be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 522 for controlling the display.

In operation, the input module 514 accepts an operator input 524 via the one or more input devices, and communicates the accepted information or selections to other components for further processing. The database module 516 organizes plans (e.g., robotic control plans, surgical plans, drone control plan, etc.), records (e.g., maintenance records, patient records, historical treatment data, etc.), surgical equipment data (e.g., instrument specifications, data usage, minimum data requirements, etc.), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to at least one database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

The systems disclosed herein can provide intra-operative surgical planning for at least partially controlling a robotic surgical apparatus (e.g., the surgical robot 440 of FIGS. 4A-4B). A method of intra-operative planning can include obtaining intraoperative patient data, performing virtual simulations to generate at least one robotic surgical action for an intra-operative surgical plan using a trained machine learning model 216 (see FIG. 2), and causing the robotic surgical apparatus to perform the at least one robotic surgical action according to the intra-operative surgical plan. The simulation can be based, at least in part, on a pre-operative surgical plan that includes, for example, treatment goals, number of treatment steps, patient information, robotic surgery functionality, etc. A robotic surgical system 160 (see FIG. 1) and/or user can select the plans, input parameters, patient data for generating the simulation.

The modules 512 can perform the simulations designed for the processor 504. The display module 524 can display the simulations, simulation input data, etc. The database module 516 can organize obtained data, simulations, and plans (e.g., pre-operative surgical plans, intraoperative surgical plans, etc.). The steps of the intraoperative simulations can be repeated to dynamically modify the intra-operative surgical plan. For example, after performing a robotic surgical action, additional intraoperative patient data is obtained. Additional intraoperative virtual simulations can be performed based on additional intraoperative patient data for an updated intra-operative surgical plan. In response to a failure to identify a robotic surgical step for the intra-operative surgical plan, the system can request and receive user input for controlling the robotic surgical apparatus. For example, if the system fails to identify a surgical step that meets one or more threshold criteria, the system can turn control over the robotic surgical apparatus to the user. Once the user performs a predefined step, or number of steps, the system can perform additional simulations to determine whether to operate in an autonomous mode, semi-autonomous mode, or another mode. Accordingly, simulations can be used to determine the mode of operation, surgical steps, predicted outcomes or event, etc. Virtual simulations of surgical procedures or portions thereof (e.g., a single surgical step, a series of surgical steps, etc.) can be scored based on predicted outcomes or events. The system or user can select a virtual simulation used to generating corresponding surgical steps for the robotic apparatus based on the score.

II. Systems, Methods, and Apparatus to Perform Latency Managed Telesurgery

Telesurgery system has a huge potential to provide healthcare surgical services to patients at remote locations using wireless communication. The telesurgery system may generally work as a master-slave system and the possibility for using the master-slave system to perform telesurgery procedures has been recognized in 2001, when the first telesurgery was conducted on a patient in Strasbourg, France, by Professor Jacques Marescaux. The telesurgery system has led to the foundation of the globalization of surgical procedures. In the telesurgery system, the surgeon at a master site performed surgery by guiding the surgical robot at the surgical site. The surgeon at the master site controlled the surgery by sending various control commands to the surgical site through a human system interface, which mainly comprised of haptic devices, headphones, and video consoles for audio-video feedback. The telesurgery system has made a significant societal impact as it fulfilled the shortage of surgeons and also eliminated geographical barriers to provide timely and high-quality surgical intervention. The telesurgery system further has prevented complications, financial burden, and often risky long-distance travel. Further, the telesurgery system has provided benefits not only to patients but also to the surgeons by ensuring their safety.

Currently, many research groups have developed experimental systems over the years. A major milestone was achieved in 2014 when Shenai et al. developed a technology based on Virtual Interactive Presence (VIP) that allowed remote neurosurgeons to collaborate with a shared 3-Dimensional (3D) display via high-definition binoculars. However, the VIP faced a drawback of having a mean latency time of 760±606 milliseconds.

Since 2014, many surgeons across the world have initiated telesurgery from far locations, but the success rate has not reached up to the mark. The reason behind not achieving success is high communication latency and overhead in the existing telesurgery system, which limits the applicability and reliability of the telesurgery system. In some embodiments, latency time may generally include the delay time in transferring auditory, visual, and even tactile feedback between two locations that may have some distance between each other. The high communication latency can be attributable to server overload, network routing problems, and congestion. The time delay not only generates a lengthy operation but also produces significant surgical inaccuracy and unreliability, which can risk the safety of the patient.

Numerous technological advancements in telesurgery systems have occurred to improve accuracy and reliability. Despite the latest improvement in the telesurgery system, high latency time continues to be a technical problem with conventional telesurgery systems. Thus, further advancement is required to develop technical solutions to lower the latency and overhead problem. A telesurgery system with latency management techniques can make telesurgery reliable, secure, and/or cost-effective, especially in certain remote locations where connectivity may be lower quality, sporadic, or otherwise insufficient to practice telesurgery. Thus, there exists a need for a latency managed telesurgery system that can overcome at least these technical problems.

FIG. 6 illustrates a system 600 for performing latency managed telesurgery, according to an embodiment. The system 600 may comprise a central hub 602, a cloud network 604, and one or more hardware components 606 coupled to the cloud network 604. The system 600 can include or be suitable for the systems discussed in connection with FIGS. 1-5.

The central hub 602 may include one or more medical device broadband drones 602a, 602b . . . 602n. The one or more medical device broadband drones 602a, 602b . . . 602n hereinafter referred to as one or more drones 602a, 602b . . . 602n may be configured to provide secure broadband over one or more geographic areas. In one embodiment, the central hub 602 may be a trusted system that may include one or more servers that can send instructions to facilitate automatic take off, landing, charging, and all other operation of the one or more drones 602a, 602b . . . 602n. in one exemplary embodiment, the one or more servers of the central hub 602 can receive signal/instruction from the module(s) described in this patent document, and in response can send instructions to the one or more drones to be sent to one or more locations associated with one or more geographical areas. In one exemplary embodiment, the central hub 602 may include ten aerial drones to cover ten major portions of a geographic area. In one embodiment, the one or more drones 602a, 602b . . . 602n may be equipped with wireless communication relay devices, transmitter, antenna to cover the one or more geographic areas. In one embodiment, the one or more drones 602a, 602b . . . 602n may be used as flying base stations or gateways to assist wireless communication to increase the coverage and/or capacity of the system 600. In another embodiment, the one or more drones 602a, 602b . . . 602n may be used as land base stations or gateways to assist wireless communication to increase the coverage and/or capacity of the system 600. It should be noted that the one or more drones generally equipped with state of the art technology such as GPS, a suite of avionic sensors, cameras, infrared cameras, wireless communication relay devices, lasers, etc., without departing from the scope of the disclosure. Each of the one or more drones 602a, 602b . . . 602n may comprise two parts, the drone and the control system. The control system of the each of the one or more drones 602a, 602b . . . 602n may comprise sensors and navigational systems. Further, the one or more drones 602a, 602b . . . 602n may be of variety of sizes, with the largest being mostly used for military purposes such as the predator drone, an unmanned aircraft which has fixed wings and is capable of take-off and landing on short runways and broadband drones to increase the capacity and coverage of the communication network. In one embodiment, the one or more drones 602a, 602b . . . 602n may create an ad hoc continuous mesh network (or wireless network) in a "best fit" location between surgical site and remote surgeons' location to provide latency managed telesurgery. In another embodiment, the one or more drones 602a, 602b . . . 602n may create the ad hoc continuous mesh network (or wireless network) in a remote operation site based on the requirement to provide the latency managed telesurgery.

The central hub 602 can manage the drones 602a, 602b . . . 602n wirelessly communicating with each other to provide a mesh network. In some embodiments, the system 600 (e.g., the computer/server associated with the system 600) can analyze surgical plans to determine telesurgery data requirements for telesurgery procedures to be concurrently or sequentially performed. The system 600 can generate a drone control plan based on the telesurgery data requirements, communication capabilities of the plurality of drones, etc. The communication capabilities can include, without limitation, range of communication, network protocols, transmission rates, etc. The drone control plan can be configured to maintain the mesh network for one or more surgical steps of the telesurgery procedure(s). In some embodiments, the system 600 can generate individual control plans for subsets of the drones 602, thereby maintaining separate networks to be individually maintained for redundancy. In some embodiments, the system 600 schedules telesurgery procedures based on network capabilities. The cloud network 604 may be coupled to the one or more hardware components 606. It should be noted that the cloud network 604 is a type of information technology (IT) infrastructure that hosts some or all of a system's network capabilities and resources in a public or private cloud platform that are managed in-house or by a service provider, and available on demand. The cloud network 604 may be implemented using a collection of server devices to provide one or more services to the coupled devices. Further, the cloud network 604 may be a wired and/or a wireless communication. The cloud network 604, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques known in the art. The communication network may allow ubiquitous access to shared pools of configurable resources and higher-level services that can be rapidly provisioned with minimal management effort, often over internet and relies on sharing of resources to achieve coherence and economies of scale, like a public utility, while third-party clouds enable organizations to focus on their core businesses instead of expending resources on computer infrastructure and maintenance.

Further, the one or more hardware components 606 may include an operating room (OR) equipment 608. In one embodiment, the OR equipment 608 may include a robotic surgery system 610, an imaging device 612, one or more sensors 614, and a communication hardware 616. The OR equipment 608 may also include an operating room interface (e.g., a display). In one embodiment, the OR equipment 608 can include the equipment discussed in connection with FIGS. 1-5, such as a robotic surgical system (e.g., surgical systems 100, 200, 300, 400, consoles (e.g., console 420), surgical robot (e.g., surgical robot 440), and a computer or data system (e.g., system 450).

The system 600 can determine data requirements for the surgical equipment, at least one safety factor for completing steps, etc. The system 600 can determine telesurgery data requirements (e.g., data transfer rates, latency limitation, etc.) based on the data requirements for concurrently used surgical equipment at the same or different locations, including multiple surgical sites. The system 600 can generate and modify drone control plans based on the telesurgery data requirements of some of all of the surgical steps. The drone control plan can include, without limitation, positioning of the plurality of drones, drone flights paths, drone flight schedules, one or more communication channels, power consumption plan for one or more the drones, throttling bandwidth, and/or communication protocols. For example, the drone control plan can be configured to maintain a sufficient number of drones operational to perform multiple steps in the surgical procedure. Drones can be added or removed from the network to manage power consumption, reduce excess network capacity, provide communication redundancy, compensate for environmental changes (e.g., weather changes), etc. The system 600 can manage resources of the drones 602a, 602b . . . 602n by determining the availability of resources that can be allocated to facilitate execution of telesurgery communications for the telesurgery procedure. The system 600 can then determine an amount of resources of the system for telesurgery actions to execute and implement one or more corrective measures to free up that amount of the resources (e.g., CPU capacity, memory, and/or communication bandwidth). The system 600 can prioritize communications for surgical steps based on priority levels (e.g., user inputted level, ML determined levels, etc.) of the one or more steps.

The operating room interface may be configured to receive controls from the remote surgeon. For example, the remote surgeon can use a console, such as the console 420 discussed in connection with FIGS. 4A and 4B. The operating room interface may further be configured to respond to the received surgical controls. In one embodiment, the operating room interface may display a warning message in case of weak network signal. Further, the robotic surgery system 610, the imaging device 612, the one or more sensors 614, and the communication hardware 616 may communicate with the cloud network 604, via the OR equipment 608.

In one embodiment, the robotic surgery system 610 may be used for carrying out desired effects or performing a surgery or operation. Further, the robotic surgery system 610 may include at least a robotic arm and an end effector. It can be noted that the robotic arm is a type of mechanical arm, usually programmable, to perform surgical procedure with more precision, flexibility and control than is possible with conventional techniques. The robotic arm may be sum of the mechanism or may be part of a more complex robot. The robotic arm may be a Cartesian robot, a collaborative robot, an anthropomorphic robot, a SCARA robot, a spherical/polar robot, an articulated robot, or a parallel robot, without departing from the scope of the disclosure. In an exemplary embodiment, the robotic arm may be manufactured by different manufacturers such as but not limited to Intuitive Surgical, Stryker, Transenterix, Embodied, SoftBank Robotics, Diligent Robotics, Barrett Technology, and Energid Technologies. In one embodiment, the robotic arm may be a serial robot arm having chain of links moved by joints which are actuated by motors. Further, robotic arms may be typically classified in terms of the number of degrees of freedom. In one embodiment, the number of degrees of freedom may be equal to the number of joints that move the links of the robotic arm. At least six degrees of freedom are required to enable the robotic hand to reach an arbitrary pose (position and orientation) in three dimensional space. Additional degrees of freedom allow to change the configuration of the link of the robotic arm. The configuration of the robotic arm may be calculated by a mathematical process called Inverse kinematics, typically in terms of joint angles, given a desired pose of the robot hand in three dimensional space.

Further, the end effector may be a peripheral device that attaches to the robotic arm allowing the robotic arm to interact with the patient's body, the surgeon, other surgical tools, or providing lighting or imaging, at any point before, during, or after a surgical procedure. In one embodiment, the end effector may be at least a surgical tool, a gripping device, a probe, an endoscope, and a scalpel. The surgical tool may allow the robotic arm to perform a specific actions or carry out desired effects during a surgery or operation, such as modifying biological tissue, or to provide access for viewing biological tissue. Further, the gripping device may allow the robotic arm to pick up and hold objects, and enable surgical staff to automate key processes, such as retrieving or returning surgical tools to a surgical tool container. In one embodiment, the probe may be a sensor that can sense parameters of a patient, such as body temperature. The scalpel may be a small and extremely sharp bladed instrument that the robotic arm may use for the surgery. In some embodiments, the robotic surgery system 610 includes one or more surgical robot, such as the surgical robot 440 of FIG. 4A.

In one embodiment, the imaging device 612 may be used to visualize physical diagnosis among physicians, surgeons, nurses, and other medical staff. Further, the imaging device 612 may allow images to be obtained from the internal structures of patient's body that are obscured by other tissues, such as skin and bones, and may be used to determine future care. In one embodiment, the imaging device 612 may include at least a magnetic resonance imaging (MRI), X-ray, a camera to detect visible light, and other imaging devices. In an exemplary embodiment, the other imaging devices may include Computed tomography (CT), Fluoroscopy, Ultrasound, Echocardiography, and Nuclear medicine, such as positron emission tomography (PET). Further, the imaging device 612 enables a set of surgical techniques that can be performed noninvasively by producing images of the internal structure of the body.

Further, the one or more sensors 614 may include at least but not limited to patient monitoring devices and operating room monitoring devices. The patient monitoring devices may include, at least, but not limited to, electroencephalogram (EEG), Electrocardiography (ECG)/(EKG), oxygen saturation from a pulse oximeter (SpO2), blood pressure, and other patient monitoring devices. Further, the operating room monitoring devices may include devices at least to control air quality, temperature, and audio. In one embodiment, Heating, ventilation, and air conditioning (HVAC) may be used to control the quality level of the air and temperature of the environment. It can be noted that goal is to provide thermal comfort and acceptable indoor air quality. HVAC may be defined as a sub-discipline of mechanical engineering, based on the principles of thermodynamics, fluid mechanics and heat transfer. Further, refrigeration is sometimes added to the field's abbreviation, as HVAC&R or HVACR or "ventilation" is dropped, as in HACR. Further, HVAC is an important part of residential structures such as single family homes, apartment buildings, hotels and senior living facilities, medium to large industrial and office buildings such as skyscrapers and hospitals, vehicles such as cars, trains, airplanes, ships and submarines, and in marine environments, where safe and healthy building conditions are regulated with respect to temperature and humidity, using fresh air from outdoors. In one embodiment, an air purifier may be used to control the quality level of the air.

The communication hardware 616 may be used to establish a communication with the remote surgeon. The communication hardware 616 may be used to give the live feed of the operating room to the remote surgeon during the telesurgery. Further, the communication hardware 616 may be positioned at the surgical site. In one embodiment, the communication hardware 616 may include at least a microphone, and network equipment at the surgical site. In one embodiment, the microphone is a transducer that converts sound into an electrical signal. In another embodiment, the microphone may employ different methods to convert the air pressure variations of a sound wave to an electrical signal. The network equipment may be used to establish the connection of the surgical site with a device/equipment associated with the remote surgeon. In one exemplary embodiment, the network equipment may include switch, hub, bridge, router, gateway, modem, repeater & access point.

Further, the one or more hardware components 606 may comprise one or more surgical controls 618. Further, the one or more surgical controls 618 may include a surgeon terminal 620, a controller 622, and a communication hardware 624. The one or more surgical controls 618 may be available with the remote surgeon to perform telesurgery. In one embodiment, the surgeon terminal 620 may include a user interface (UI) to allow the remote surgeon to view patient data. Further, the surgeon terminal 620 may allow the remote surgeon to view one or more data related to the patient from a medical database, via cloud network 604, which may be explained in FIG. 7. Further, the surgeon terminal 620 may allow the remote surgeon to monitor live feed from the OR. In addition, the surgeon terminal 620 may allow the remote surgeon to take any audio and/or video from the surgical site or the OR.

Further, the controller 622 may be used to process the control signals that the remote surgeon may receive during the telesurgery. In one embodiment, the controller 622 may be a digital signal controller (DSC) for processing the control signals received during the telesurgery. The DSC may be a hybrid of microcontrollers and digital signal processors (DSPs). In another embodiment, the controller 622 may be a microcontroller to process the control signals received during the telesurgery. The controller 622 may be manufactured by different manufacturers such as Microchip, Freescale, and Texas Instruments. Further, the controller 622 may also include haptics. Haptics may also be known as kinaesthetic communication or 3D touch which refers to any technology that can create an experience of touch by applying forces, vibrations, or motions to the user. Further, haptics may be enabled by various haptic devices which works on force feedback by means of which the remote surgeon gains information of resistance and sensation on some part of the body. Non-limiting surgical controls are discussed in connection with FIGS. 4A and 4B.

In one embodiment, the communication hardware 624 may be used to establish communication between the surgical site and the remote surgeon's location/site, monitoring from a distant to take input from the operating room and send surgical control signals. The communication hardware 624 may be used at the remote surgeon side. In one embodiment, the communication hardware 624 may include audio and/or visual support. Further the communication hardware 624 may also include a microphone, and network equipment at the remote surgeon site.

Further, the one or more hardware components 606 may comprise a transmission hardware 626. Further, the transmission hardware 626 may correspond to electronic devices which may be required for communication and interaction between devices placed at two different locations. In one embodiment, the transmission hardware 626 may comprise a remote surgeon transceiver 628, one or more server/relay stations 630, one or more mobile relay stations 632, and an operating room transceiver 634. Further, the remote surgeon transceiver 628, the one or more server/relay stations 630, the one or more mobile relay stations 632, and the operating room transceiver 634 may be in communication with the cloud network 604 via the one or more hardware components 606.

The remote surgeon transceiver 628 may facilitate transmitting and receiving surgical signals. In one embodiment, the remote surgeon transceiver 628 may be a router or a modem which facilitates sending the remote surgeon's input to the OR. Further, the remote surgeon transceiver 628 may be an origin point of the remote surgeon's input. It can be noted that the remote surgeon transceiver 628 may be the destination of the data being received from the operating room. Further, the remote surgeon transceiver 628 may convert the input of the remote surgeon into electrical signals, to be communicated over the cloud network 604.

Further, the one or more server/relay stations 630 may include a fixed network infrastructure to relay, repeat and/or boost the signal send by the remote surgeon transceiver 628. The one or more server/relay stations 630 may be wired or wireless. Further, the one or more server/relay stations 630 may include an additional processor or computation device as per requirement. The additional processor or computation device may include supercomputer, edge computing device, and other data processing devices. It should be noted that the supercomputer can be a computer with a high level of performance as compared to a general-purpose computer and are used for a wide range of computationally intensive tasks in various fields, including quantum mechanics, weather forecasting, climate research, etc. Also, it can be noted that edge computing may be a distributed computing paradigm that brings computation and data storage closer to the sources of data. Thus, edge computing may be expected to improve response times and save bandwidth. The additional processor or computation device may further include databases and other data sources.

Further, the one or more mobile relay stations 632 may refer to a drone mesh network (or wireless network). In one embodiment, the one or more mobile relay stations 632 may be an air based station hovering on the required geographic area. In another embodiment, the one or more mobile relay stations 632 may be land based station placed on the required geographic area. In yet another embodiment, the one or more mobile relay stations 632 may be sea based station. In yet another embodiment, the one or more mobile relay stations 632 may be placed on low earth orbit. Further, the one or more mobile relay stations 632 may have a capability to function like a server or as repeater nodes. The operating room transceiver 634 may be a router or a modem to transmit and receive surgical signals. It should be noted that the operating room transceiver 634 may be placed at the surgical site to send the data originated in the operating room equipment to the remote surgeon. Further, the operating room transceiver 634 may be an origin point of operating room inputs. Furthermore, the operating room transceiver 634 may be a destination of the surgical controls, which may convert the electrical signals for controlling the surgical tools in the operating room.

In one embodiment, the telesurgery third party cloud network 636 may be a cloud network managed by externally, by a third party. Further, the telesurgery third party cloud network 636 may enable the system 600 to offer secured services from highly skilled trained staff. The telesurgery third party cloud network 636 may comprise a base module 638, which may further include one or more modules such as, but not limited to, a scheduling module 640, an equipment setup module 642, a setup module 644, a Wi-Fi network module 646, and an operation module 648. In an additional embodiment, the base module 638 may include a mobile network test module (not shown) along with the one or more modules.

The system 600 may further comprise a medical database 650 for storing one or more patient data and the one or more surgery data, as shown in FIG. 7. In one embodiment, the one or more patient data may include at least but not limited to name, age, weight, diagnosis, patient images, and medical history of the patient's family. Further, the one or more surgery data may include at least but not limited to real time imaging data, pre-plan for surgery, type of surgery, surgical site, and expected outcome. In an exemplary embodiment, the surgery data may include data for patient Alex, who is 34 years old and weighs 74 kilograms. Further, Alex is diagnosed with a fracture on his left leg and has images—Image 1, Image 2, and Image 3 from his X-rays and MRIs. Further the family history for Alex includes high blood pressure from Alex's mother, diabetes from Alex's father, and Alex's grandfather died of kidney cancer. In addition, the real-time imaging data for Alex includes image of Alex's left leg, an MRI scan, and X-ray image of Alex's left leg. Further, a pre-plan for operation on Alex includes medication for numbing the left leg. The type of operation is surgical operation for fracture. Further the surgical site is lower portion of left leg and the expected outcome is a stable left leg with no pain and no side-effects—including normal blood pressure.

The telesurgery third party cloud network 636 may be communicatively coupled to the base module 638. The base module 638 may be configured to receive a request to schedule a telesurgery procedure. Further, the base module 638 may use the scheduling module 640 for performing the telesurgery procedure. In one embodiment, the scheduling module 640 may be configured to define the need for broadband access for the telesurgery procedure in the one or more geographic area. For example, for performing a telesurgery procedure for a fractured leg of Alex who situated in Fairbanks, by his remote surgeon Dr. T who is situated in a telesurgery environment in California. In one embodiment, the scheduling module 640 may be further configured to schedule a particular time for using the wireless communication and agree on the scheduled time with the remote surgeon and the surgical site for the telesurgery procedure. Further, the scheduling module 640 may be configured to define one or more parameters including, but not limited to, type of operation, number of surgeons, and types of surgeon needed at remote site and the surgical site. For this example, the scheduling module 640 defines that the type of operation is a screw insertion in Alex's left leg, number of surgeons required at surgical site is two, number of surgeons required at remote site is one. Further, the scheduling module 640 may be configured to define a number of mobile relay stations, allocating bandwidth, and selecting locations for the mobile relay stations. For example, the scheduling module 640 defines 2 mobile relay stations and a bandwidth of 10 MHz. Furthermore, the scheduling module 640 may be configured to determine the requirement of the bandwidth needed and expected latency. For example, for the telesurgery procedure on Alex, a bandwidth of 10 MHz and an expected latency of ±70 milliseconds.

In some embodiment, the medical database 650 include a telesurgery surgical plan. The system can perform on or more simulations can be used to generate, modify, and/or verify data settings, expected latency, etc. In some embodiments, control plan for drones is selected based on the simulations. For example, multiple simulations can be performed for different drone-managed network configurations using CNN, machine-learning engines. The healthcare provider can select the surgical plan, surgical equipment, drone settings, etc. based, at least in part, on the simulations.

In an optional embodiment, the base module 638 may trigger a mobile network test module (not shown). The mobile network test module may be operational before performing the telesurgery procedure. Further, the mobile network test module may measure the latency of the wireless communication established between the surgical site and the remote surgeon's site. Further, the mobile network test module may send a signal to the central hub 602 to trigger the central hub 602 to send out the one or more drones 602a, 602b . . . 602n to various locations needed for the surgery. For example, for Alex's telesurgery procedure, the mobile network test module may send signals that trigger the drones to be sent between Anchorage and Fairbanks, to providing connection between Fairbanks and California. The mobile network test module may further measure environmental factors, network factors, and all other factors affecting the latency/bandwidth of the wireless communication. For example, factors affecting the latency include weather and/or wind speed.

In an example embodiment, the mobile network test module can use a pre-determined table to determine the effect of weather/wind speed on latency. For example, if the mobile network test module determines a temperature in an area and determines from the pre-determined table that the effect of that temperature on latency is high, then the mobile network test module can send this information to the base module 638. In another example, if the mobile network test module determines a wind speed in an area and determines from the pre-determined table that that wind speed is within a range of wind speeds that is associated with high latency, then the mobile network test module can send this information to the base module 638. In response to receiving the information about the effect of weather/wind on latency, the base module 638 can send a signal to the mobile network test module to trigger the mobile network test module to send a signal to a computer/server associated with the central hub 602 to send additional drones to keep latency low and/or to decrease a distance between at least two drones.

In this patent document, a measured/determined latency of a wireless network may be the same as a latency of a network that includes the wireless network, where the network may include a starting point/node for a data to be transmitted to an ending point/node, and where the data is communicated by one computer/device associated with a surgical site to another computer/device associated with a location of the remote physician/surgeon.

Further, the base module 638 may further trigger the equipment setup module 642. The equipment setup module 642 may be configured to query the medical database 650 to find equipment available for the surgery, based on the type of operation. For example, for telesurgery procedure for Alex's left leg, equipment available is Ilizarov apparatus. Further, the equipment setup module 642 may be configured to send details of the equipment available to the remote surgeon. For example, the equipment setup module 642 sends details of Ilizarov apparatus to Dr. T. In one embodiment, the equipment setup module 642 may send the details of hardware components 606 like surgical controls required with the remote surgeon and operation room equipment at the remote surgeon side. Further, the remote surgeon may approve the equipment available or modify the surgical location until both the remote surgeon and the surgical site agrees. It can be noted that the selection of the location may be based on the required equipment or availability of similar type of equipment. After approval from the remote surgeon, the equipment setup module 642 may determine maximum allowable latency based at least on type of equipment and surgical locations. For example, the equipment setup module 642 determines that a maximum latency of 100 milliseconds is allowed.

After determination by the equipment setup module 642, the base module 638 may trigger the setup module 644, which is configured to ensure availability of the equipment at the surgical site and with the remote surgeon. In one embodiment, the setup module 644 may ensure the availability of control equipment with the remote surgeon and the surgical devices (operating room equipment as disclosed in FIG. 6) on the surgical site. For example, the setup module 644 ensures that the Ilizarov apparatus is available at surgical site in Fairbanks and a mobile interface is available with Dr. T in California. The base module 638 may ensure if all the hardware components like the robotic surgery system 610, the imaging device 612, the one or more sensors 614 and communication hardware 616 are available at the surgical site. The setup module 644 may further ensure the availability of the surgical controls like the surgeon terminals 620, the controller 622 and the communication hardware 624 with the remote surgeon.

After ensuring the availability of equipment, the base module 638 may trigger the Wi-Fi network module 646. The Wi-Fi network module 646 may be used to create a Wi-Fi network within the surgical site and the location of the remote surgeon. In one embodiment, the Wi-Fi network may use multiple parts of the IEEE 802 protocol family and to interwork seamlessly with the wired Ethernet. The Wi-Fi network may use 2.4 gigahertz (120 mm) UHF and 5 gigahertz (60 mm) SHF radio bands. In one embodiment, the Wi-Fi network module 646 may be configured to deploy the one or more drones 602a, 602b . . . 602n on the selected location to create the Wi-Fi network. For example, the Wi-Fi network module 646 sends signal(s) to deploy drones between Fairbanks, Ak. and Anchorage, Ak., to connect the surgical site in Fairbanks to the remote surgeon in California, in such an example, Anchorage may have a sufficiently capable network for telesurgery, but the Fairbanks network may have latency that is too high for telesurgery. It can be noted that the one or more drones 602a, 602b . . . 602n may physically land at a designated location or may hover over the designated location. Further, the Wi-Fi network module 646 may be configured to ensure continuous network connection and adequate latency. In one embodiment, the Wi-Fi network module 646 may add other drones in the network created by the one or more drones 602a, 602b . . . 602n to maintain the adequate latency. Further, the one or more drones 602a, 602b . . . 602n may ping the telesurgery third party cloud network 636 for determining a check on latency of the network formed by using the one or more drones 602a, 602b . . . 602n. It can be noted that when Wi-Fi network module 646 or the base module 638 receives the latency and determines that the latency is too high (e.g., by determining that the latency is greater than a maximum allowable latency), the Wi-Fi network module 646 may send a signal to the central hub 602 to add another drone in the network. For example, when the base module 638 or the Wi-Fi network module 646 determines that the latency is 150 milliseconds and is greater than the maximum allowable latency, then the Wi-Fi network module 646 may send a signal to the computer associated with the central hub 602 to send/deploy additional drones. If, for example, the first drones are located near Healy, Ak. and Talkeetna, Ak., the Wi-Fi network module 646 adds another drone near Denali Park and Willow, Ak. It can be noted that the telesurgery connection between the remote surgeon and the surgical site may be initiated, for example, by the base module 638, only after the adequate latency is maintained as determined by the base module 638. For example, the telesurgery connection is initiated by the base module 638 when the base module 638 determines that latency is less than the maximum allowable latency (e.g., 100 milliseconds). In another example, the base module 638 can determine that an adequate latency is maintained by determining that the measured latency is less than a maximum allowable latency for more than a certain time period that may be pre-determined. In this example, after the base module 638 has determined that the adequate latency is maintained, the base station 638 can initiate the telesurgery connection.

When the telesurgery connection is initiated, the base module 638 may trigger the operation module 648. The operation module 648 may send signal(s) to turn the equipment on. Further, the operation module 648 may comprise a test equipment. In one embodiment, the test equipment may be used to check the audio and video connections and one or more sensors including, but not limited to, $SpO_2$ sensor, temperature sensor, and heart rate sensor. Further, the operation module 648 may comprise a real time communication module. In one embodiment, the real time communication module may be used to send the audio, video, and sensors data to the remote surgeons and the surgical controls 618 to the surgical site. For example, the real time communication module may share a real time video of the telesurgery procedure with Dr. T. Further, the operation module 648 may comprise an operation recording module. In one embodiment, the operation recording module may be configured to record one or more data associated with the surgery. It can be noted that the recorded one or more data associated with the surgery may be stored in the medical database 650. In one embodiment, the surgical interface may be configured to display the one or more data associated with the surgery to the remote surgeon. It can be noted that the operation of the base module 638 may be explained in FIG. 8A and FIG. 8B.

Figure 8A:
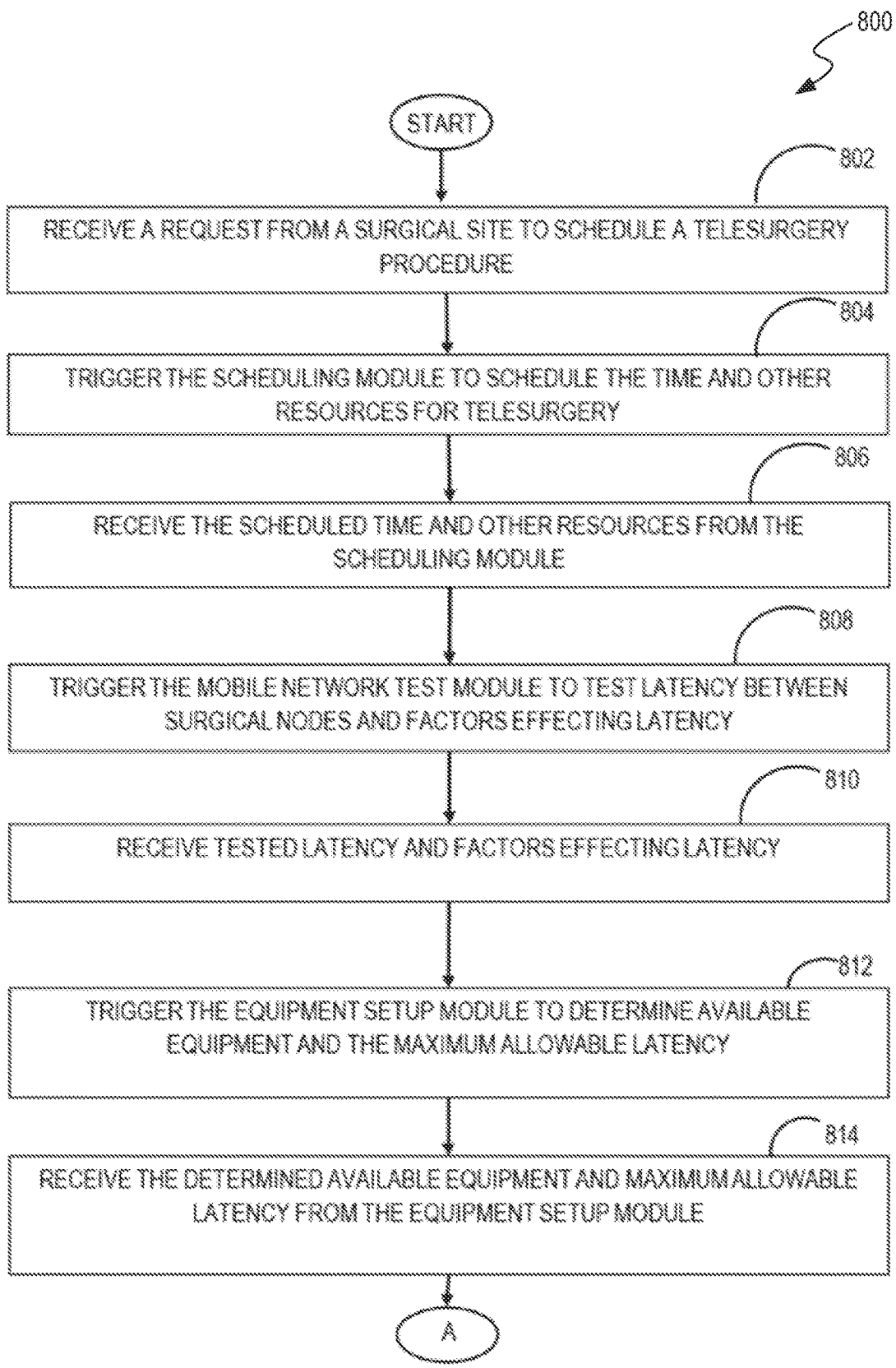
FIG. 8A illustrates a flow chart showing a method of operation of a base module in the system, according to an embodiment.
Figure 8B:
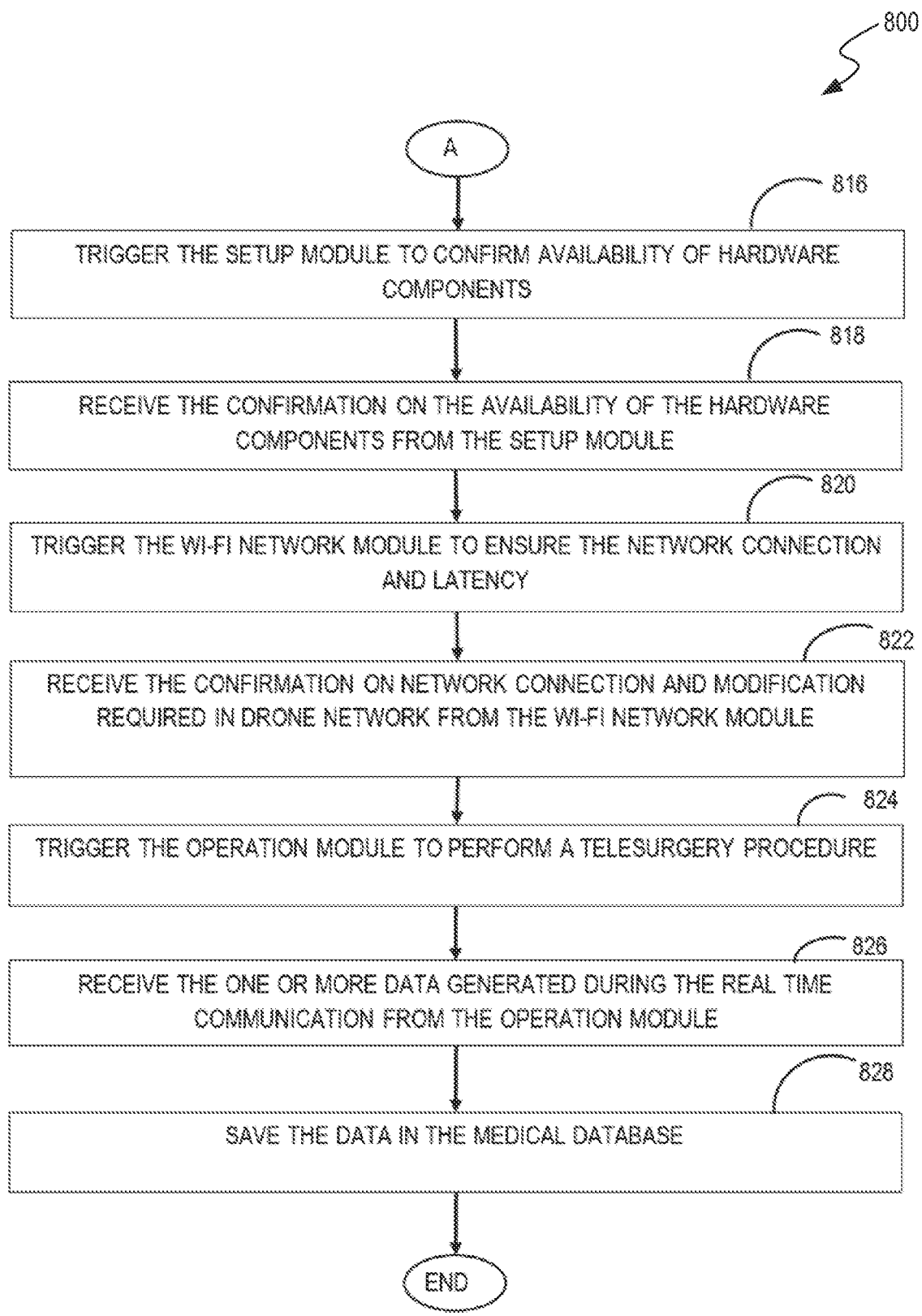
FIG. 8B illustrates a flow chart showing the method of operation of the base module in the system, according to an embodiment.

FIG. 8A and FIG. 8B illustrate a flow chart 800 showing a method of operation of the base module 638 in the system 600, according to an embodiment. FIG. 8A ad FIG. 8B are explained in conjunction with FIG. 9, FIG. 10, FIG. 11, FIG. 12, and FIG. 13. It should also be noted that in some alternative implementations, the functions noted in the blocks may occur out of the order noted in the drawings. For example, two blocks shown in succession in FIG. 8A and FIG. 8B may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 800 starts at step 802 and proceeds to step 828. At first, the base module 638 may receive a request from the surgery site to schedule a telesurgery procedure, at step 802. In one exemplary embodiment, the base module 638 receives a request for scheduling the telesurgery for fractured left leg of Alex in Fairbanks on Sep. 20, 2021, with remote surgeon—Dr. T located in California.

Successively, the base module 638 may trigger the scheduling module 640 to schedule a time and other resources related to the telesurgery procedure, at step 804. Further, the other resources may refer to the operation type, number and type of doctors needed, the hardware requirements, mobile relay points, allocating bandwidth, locations for mobile relay points, bandwidth needed, and expected latency during the telesurgery procedure. In one embodiment, the base module 638 may send one or more surgery data to the scheduling module 640 for scheduling the time of the surgery and other resources. Further, the one or more surgery data may include at least but not limited to real time imaging data, pre-plan for surgery, type of surgery, surgical site, and expected outcome. In an exemplary embodiment, the surgery data may include data for patient Alex, who is 34 years old and weighs 74 kilograms. Further, Alex is diagnosed with a fracture on his left leg and has images—Image 1, Image 2, and Image 3 from his X-rays and MRIs. Further the family history for Alex includes high blood pressure to Alex's mother, diabetes to Alex's father, and Alex's grandfather died of kidney cancer. In addition, the real-time imaging data for Alex includes image of Alex's left leg, an MRI scan, and X-ray image of Alex's left leg. Further, a pre-plan for operation on Alex includes medication for numbing the left leg. The type of operation is surgical operation for fracture. Further the surgical site is lower portion of left leg and the expected outcome is a stable left leg with no pain and no side-effects—including normal blood pressure. It can be noted that the operation of the scheduling module 640 is explained in FIG. 9.

Figure 9:
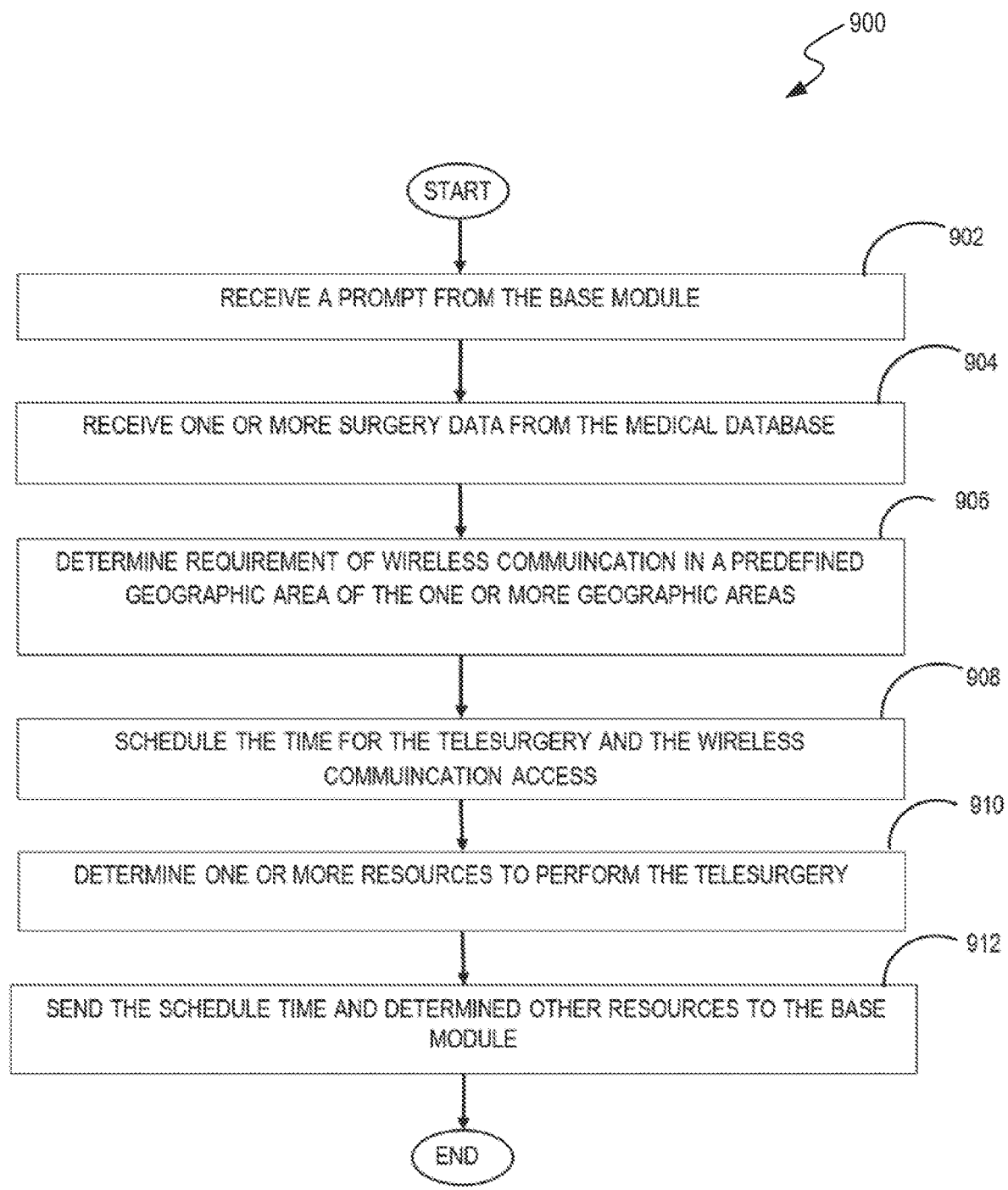
FIG. 9 illustrates a flow chart showing a method of operation of a scheduling module in the system, according to an embodiment.

FIG. 9 illustrates a flowchart 900 showing a method of operation of the scheduling module 640, according to an embodiment. It should also be noted that in some alternative implementations, the functions noted in the blocks may occur out of the order noted in the drawings. For example, two blocks shown in succession in FIG. 9 may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 900 starts at step 902 and proceeds to step 912.

At first, the scheduling module 640 may receive a prompt from the base module 638 to time and other resources related to the telesurgery procedure, at step 902. In one exemplary embodiment, the scheduling module 640 may receive a prompt to schedule the telesurgery for Alex diagnosed with left leg fracture. Successively, the scheduling module 640 may receive one or more surgery data from the medical database 650, at step 904. In one embodiment, the one or more surgery data may include at least but not limited to real time imaging data, pre-plan for surgery, type of surgery, surgical site, and expected outcome. In an exemplary embodiment, the surgery data may include data for patient Alex, who is 34 years old and weighs 74 kilograms. Further, Alex is diagnosed with a fracture on his left leg and has images—Image 1, Image 2, and Image 3 from his X-rays and MRIs. Successively, the scheduling module 640 may determine requirement of wireless communication in a predefined geographic area of the one or more geographic areas to perform the telesurgery, at step 906. In an exemplary embodiment, the scheduling module 640 determines requirement of wireless communication between the Fairbanks city and the California in order to perform the telesurgery on Alex's injured left leg. Successively, the scheduling module 640 may schedule the time for the telesurgery and the wireless communication to perform the telesurgery, at step 908. For example, the scheduling module 640 schedules the telesurgery procedure to be performed at 2 pm on Sep. 20, 2021.

Successively, the scheduling module 640 may determine one or more requirement, provisioning data, expected latency required to perform the telesurgery based on the received one or more surgery data, at step 910. In one embodiment, the one or more requirement may include number of doctors, type of doctors, and hardware requirement in surgical site and with the remote surgeon and the provisioning data may include number of mobile relay stations, allocating bandwidth, and locations of the mobile relay stations. In one embodiment, the expected latency may be determined by the quality or resolution of the video and the time delay in receiving the video at the destination. For this example, the scheduling module 640 defines that the type of operation is a screw insertion in Alex's left leg, number of surgeons required at surgical site is two, number of surgeons required at remote site is one. Further, the scheduling module 640 may be configured to define a number of mobile relay stations, allocating bandwidth, and selecting locations for the mobile relay stations. For example, the scheduling module 640 defines 2 mobile relay stations and a bandwidth of 10 MHz. Furthermore, the scheduling module 640 may be configured to determine the requirement of the bandwidth needed and/or expected latency. For example, for the telesurgery procedure on Alex, a required bandwidth of 10 MHz and/or an expected latency of ±70 milliseconds. Thereafter, the scheduling module 640 may send the determined one or more requirement, provisioning data, and expected latency required for the telesurgery to the base module 638, at step 912.

Successively, the base module 638 may receive the scheduled time, determined one or more requirement, and expected latency for the telesurgery, from the scheduling module 640, at step 806. In an exemplary embodiment, the base module 638 may receive schedule for performing the telesurgery procedure at 2 pm on Sep. 20, 2021 and the requirements of one surgeon at the remote site and two surgeons at the surgical site for surgical operation for leg fracture, requiring Ilizarov apparatus, robotic arm and end-effectors, MRI, X-RAY, and blood pressure sensors at the surgical site and surgical controls 618 with the remote surgeon and the expected latency is ±70 milliseconds.

Based on the determined schedule time and other resources, the base module 638 may trigger the mobile network test module, at step 808. It can be noted that the mobile network test module may be used to test latency between surgical nodes and factors affecting the latency. For example, the mobile network test module tests latency between the surgical site in Fairbanks and the remote site in California. It can be noted that the operation of the mobile network test module is explained in FIG. 10.

Figure 10:
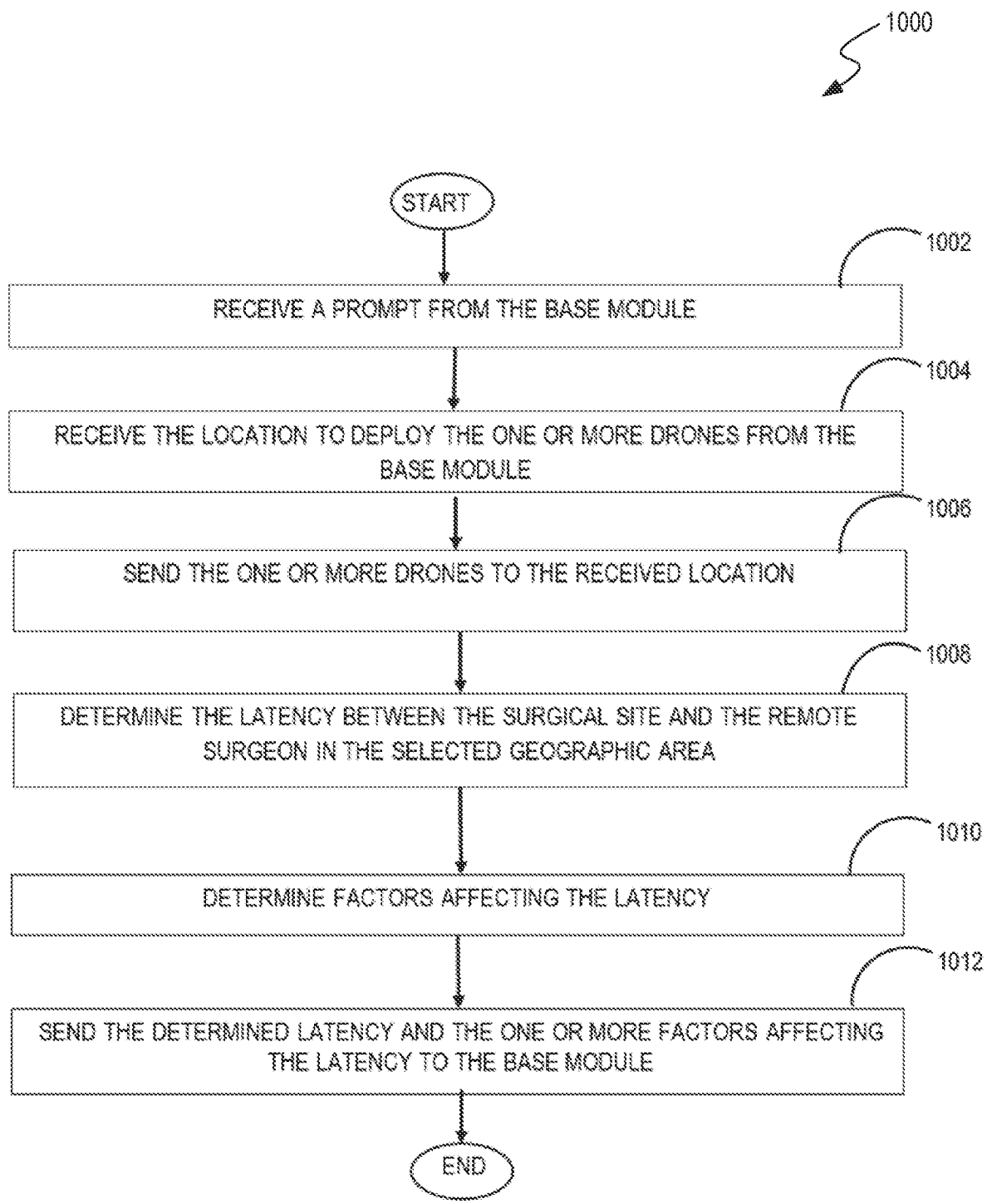
FIG. 10 illustrates a flow chart showing a method of operation of a mobile network test module in the system, according to an embodiment.

FIG. 10 illustrates a flow chart 1000 showing a method of operation of a mobile network test module, according to an additional embodiment. It should also be noted that in some alternative implementations, the functions noted in the blocks may occur out of the order noted in the drawings. For example, two blocks shown in succession in FIG. 10 may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 1000 starts at step 1002 and proceeds to step 1012.

The mobile network test module may activate before starting the telesurgery to test the network connection. At first, the mobile network test module (not shown in FIG. 6) may receive a prompt from the base module 638 to test latency in the wireless communication, at step 1002. Successively, the mobile network test module may receive the location to deploy the one or more drones from the base module 638, at step 1004. In one embodiment, the base module 638 may receive the location from the scheduling module 640. Successively, the mobile network test module may send receive the location from the base module 638 and may send instructions to the central hub 602 to send the one or more drone to the received location, at step 1006. Further, the mobile network test module may send instructions to the central hub 602 to send out the one or more drones 602a, 602b . . . 602n to various locations needed for the surgery. For example, for Alex's telesurgery procedure, the mobile network test module may send out drones deploys drones between Fairbanks, Ak. and Anchorage, Ak., to connect the surgical site in Fairbanks to the remote surgeon in California. Successively, the mobile network test module may determine the latency between the surgical site and the remote surgeon in the selected geographic area, at step 1008. For example, for Alex's telesurgery procedure, the mobile network test module tests latency between Fairbanks and California is 150 milliseconds. Successively, the mobile network test module may determine one or more factors affecting the latency, at step 1010. In one embodiment, the one or more factors may include at least but not limited to environmental factors and network factors affecting the latency of the wireless communication. For example, factors affecting the latency include weather and/or wind speed as explained in this patent document. Thereafter, the scheduling module 140 may send the determined latency and the one or more factors (and/or information related to the one or more factors such as weather/wind as explained in this patent document) affecting the latency to the base module 638, at step 1012.

Further, the base module 638 may receive the tested latency and factors affecting latency from the mobile network test module, at step 810. Further, the base module 638 may trigger the equipment setup module 642 to determine the available equipment and maximum allowable latency, at step 812. It can be noted that the operation of the equipment setup module 642 is explained in FIG. 11.

Figure 11:
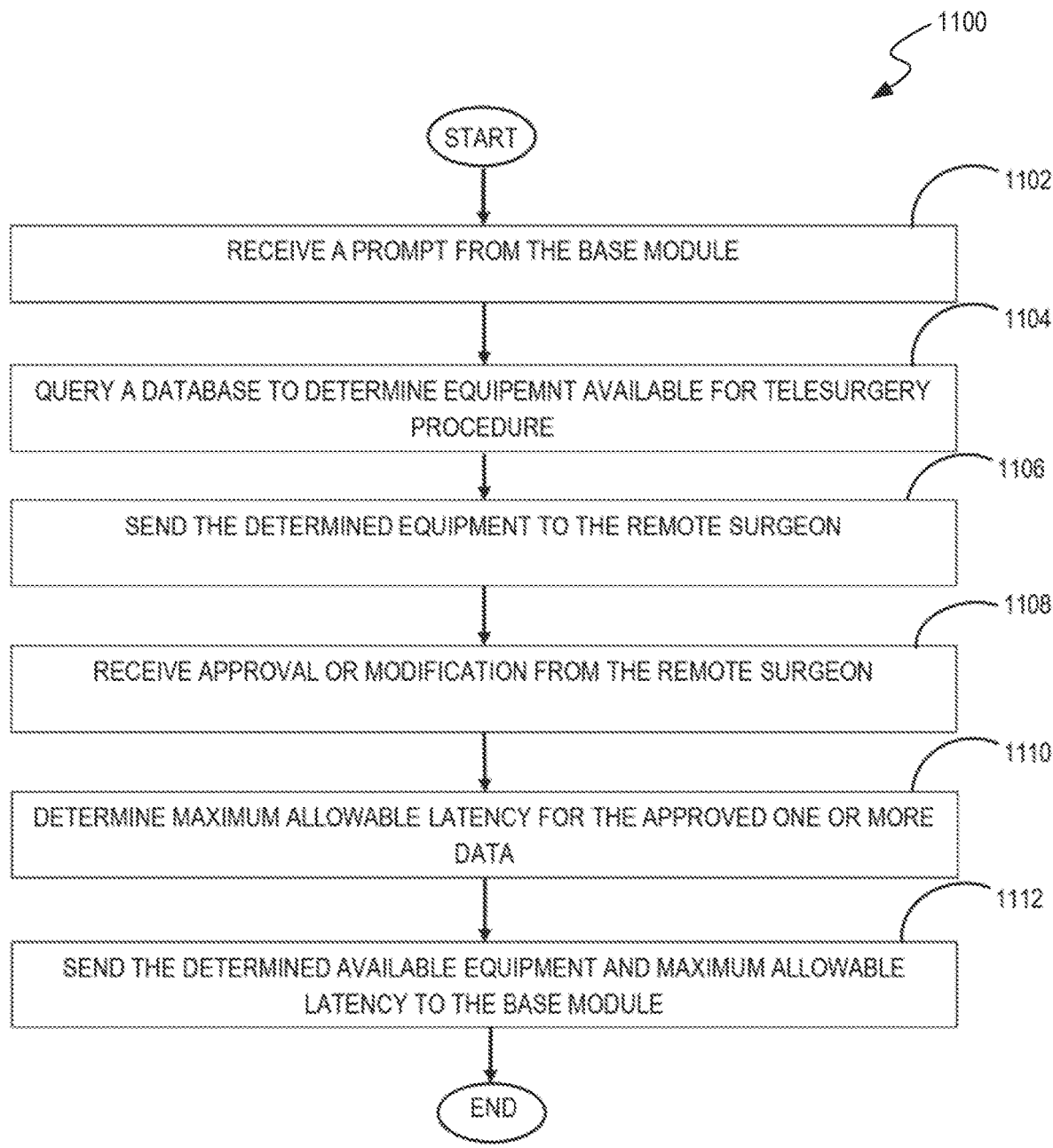
FIG. 11 illustrates a flow chart showing a method of operation of an equipment setup module in the system, according to an embodiment.

FIG. 11 illustrates a flowchart 1100 showing a method of operation of the equipment setup module 642, according to an embodiment. It should also be noted that in some alternative implementations, the functions noted in the blocks may occur out of the order noted in the drawings. For example, two blocks shown in succession in FIG. 11 may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 1100 starts at step 1102 and proceeds to step 1112.

At first, the equipment setup module 642 may receive a prompt from the base module 638, at step 1102. It can be noted that the equipment setup module 642 may be triggered to determine the available equipment and maximum allowable latency. Successively, the equipment setup module 642 may query the medical database 650 to determine the equipment available for telesurgery procedure, at step 1104. In one embodiment, the one or more data may include at least but not limited to type hardware components, availability of the hardware components, surgical location etc. based on the type of surgery. For example, for telesurgery procedure for Alex's left leg, equipment available is Ilizarov apparatus. Successively, the equipment setup module 642 may send the received one or more data to the base module 638 for approval of the remote surgeon and the surgical site, at step 1106. For example, the equipment setup module 642 sends details of Ilizarov apparatus to Dr. T for his approval. Further, the equipment setup module 642 may receive an approval or a modification related to the equipment from the remote surgeon, at step 1108. In one embodiment, the remote surgeon may approve the available equipment. For example, Dr. T approves the use of Ilizarov apparatus. In another embodiment, the remote surgeon may suggest a modification related to the equipment. For example, Dr. T suggests use of screw insertion for the telesurgery procedure on Alex. Successively, the equipment setup module 642 may determine maximum allowable latency based on the approved one or more data, at step 1110. For example, the equipment setup module 642 determines that a maximum latency of 100 milliseconds is allowed. Thereafter, the equipment setup module 642 may send the determined available equipment and determined maximum allowable latency based on the approved one or more data to the base module 638, at step 1112.

Successively, the base module 638 may receive the determined available equipment and maximum allowable latency, from the equipment setup module 642, at step 814. In an exemplary embodiment, the base module 638 receives that the determined allowable equipment is Ilizarov apparatus and the determined maximum allowable latency of 100 milliseconds. Successively, the base module 638, may trigger the setup module 644 to ensure the availability of the hardware components 606, at step 816. It can be noted that the operation of the setup module 644 is explained in conjunction with FIG. 12.

Figure 12:
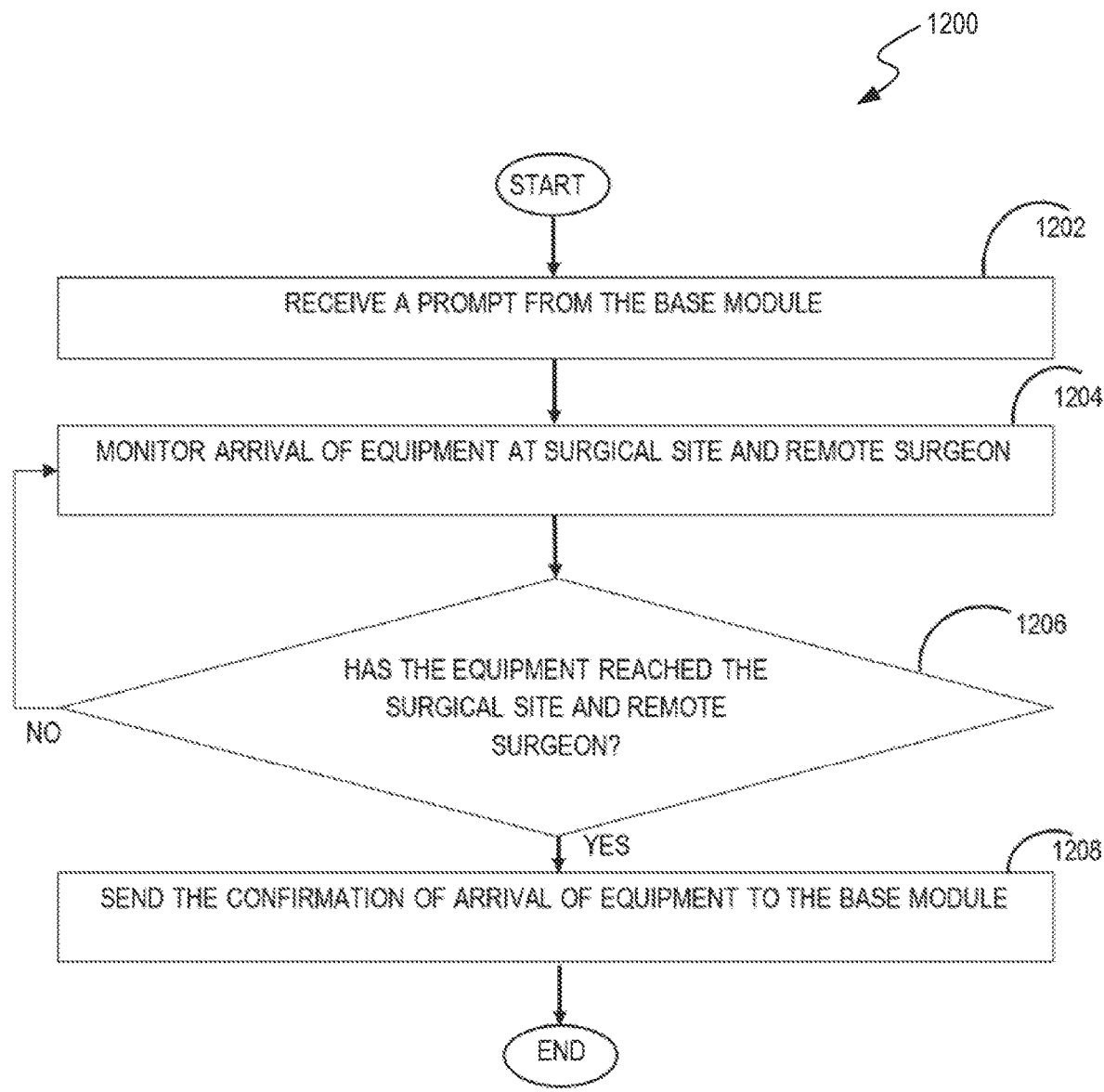
FIG. 12 illustrates a flow chart showing a method of operation of a setup module in the system, according to an embodiment.

FIG. 12 illustrates a flowchart 1200 showing a method of operation of the setup module 644, according to an embodiment. It should also be noted that in some alternative implementations, the functions noted in the blocks may occur out of the order noted in the drawings. For example, two blocks shown in succession in FIG. 12 may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 1200 starts at step 1202 and proceeds to step 1208.

At first, the setup module 644 may receive a prompt from the base module 638, at step 1202. It can be noted that the setup module 644 may be triggered to ensure the availability of the hardware components 606 like equipment at surgical site and the site of remote surgeon. Successively, the setup module 644 may monitor the arrival of the equipment at the surgical site and with the remote surgeon, at step 1204. For example, the setup module 644 monitors arrival of Ilizarov apparatus, robotic arm and end-effectors, MRI, X-RAY, and blood pressure sensors at the surgical site in Fairbanks and surgical controls 618 with the remote surgeon in California. The setup module 644 may check that the equipment has reached the surgical site and site of the remote surgeon, at step 1206. In one case, if the equipment has not reached the surgical site and site of the remote surgeon, then the setup module 644 may move to step 1204 and continue monitoring the arrival of eequipment at the surgical site and with the remote surgeon. In another case, if the equipment has reached surgical site and site of the remote surgeon, then the setup module 644 may send the confirmation on availability of the equipment to the base module 638, at step 1208. For example, with the arrival of Ilizarov apparatus, robotic arm and end-effectors, MRI, X-RAY, and blood pressure sensors at the surgical site in Fairbanks and surgical controls 618 with the remote surgeon in California, the setup module 644 sends the confirmation on availability of the Ilizarov apparatus to the base module 638.

Successively, the base module 638, may receive the confirmation on the availability of the hardware components 606 from the setup module 644, at step 818. In an exemplary embodiment, the base module 638 may receive the confirmation on the availability of the Ilizarov apparatus, robotic arm and end-effectors, MRI, X-RAY, and blood pressure sensors at the surgical site and surgical controls 618 with the remote surgeon. Successively, the base module 638, may trigger the Wi-Fi network module 646 to ensure or determine the network connection and latency, at step 820. It can be noted that the operation of the Wi-Fi network module 646 is explained in FIG. 13.

Figure 13:
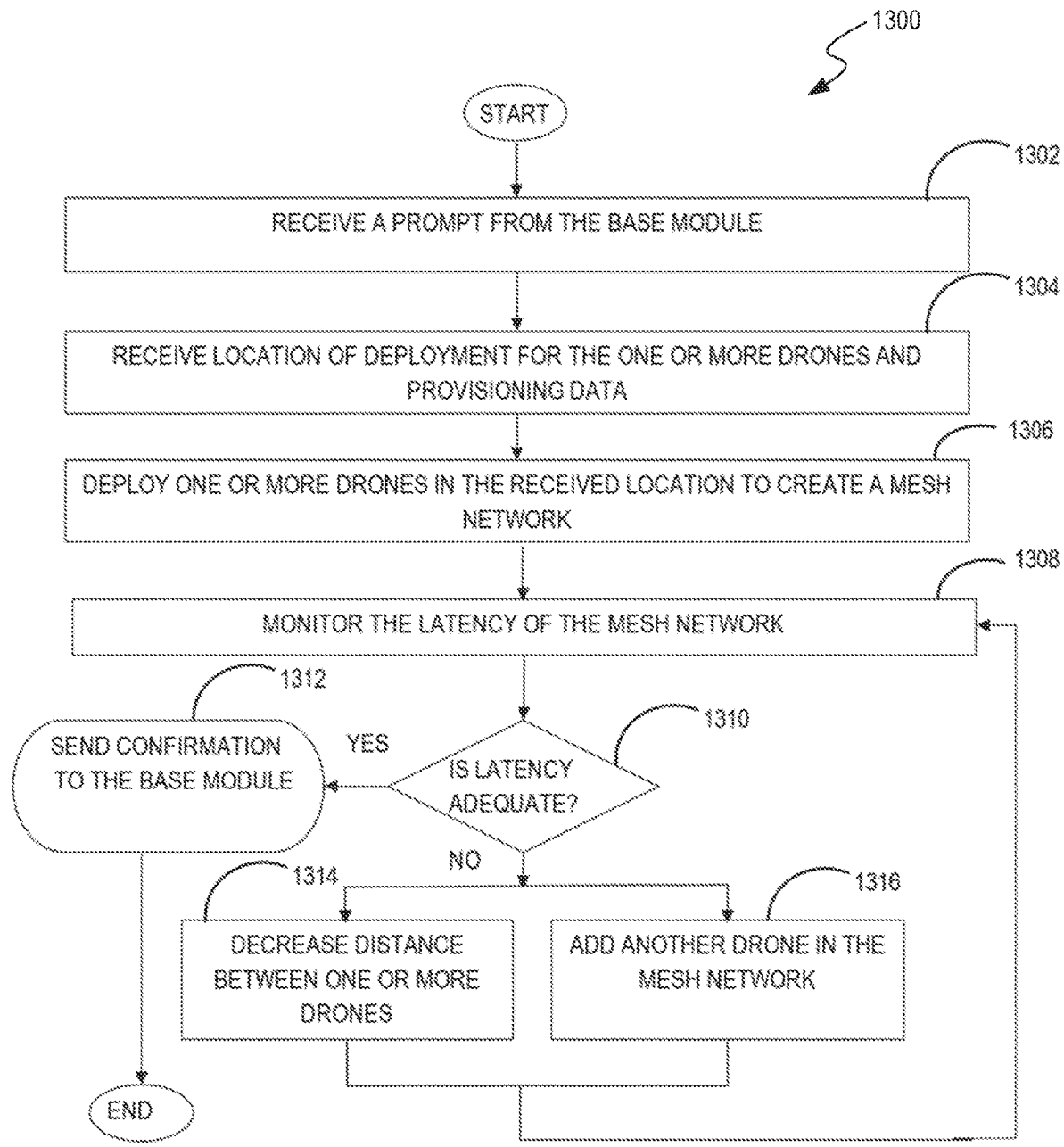
FIG. 13 illustrates a flow chart showing a method of operation of a Wi-Fi network module in the system, according to an embodiment.

FIG. 13 illustrates a flowchart 1300 showing a method of operation of the Wi-Fi network module 646, according to an embodiment. It should also be noted that in some alternative implementations, the functions noted in the blocks may occur out of the order noted in the drawings. For example, two blocks shown in succession in FIG. 13 may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 1300 starts at step 1302 and proceeds to step 1316.

At first, the Wi-Fi network module 646 may receive a prompt from the base module 638, at step 1302. Successively, the Wi-Fi network module 646 may receive the location of deployment for the one or more drones and other provisioning data from the base module 638, at step 1304. In one embodiment, the provisioning data may include the number of mobile relay stations, allocating bandwidth, and selected locations for the mobile relay stations. Successively, the Wi-Fi network module 646 may deploy the one or more drones in the selected location, at step 1306 to create a mesh network (or wireless network). For example, the Wi-Fi network module 646 deploys drones between Fairbanks, Ak. and Anchorage, Ak., to connect the surgical site in Fairbanks to the remote surgeon in California. In one embodiment, the one or more drones may physically land over the selected location. In another embodiment, the one or more drones may hover over the selected location. Successively, the Wi-Fi network module 646 may monitor the latency of the mesh network (or wireless network), at step 1308. For example, Wi-Fi network module 646 determines that the latency of the mesh network (or wireless network) over Fairbanks to California is 150 milliseconds. In one embodiment, the one or more drones may ping the network connection to determine the latency of the mesh network (or wireless network). Successively, the Wi-Fi network module 646 may determine if the latency is adequate (e.g., the Wi-Fi network module 646 may determine whether the latency is less than a threshold (e.g., maximum allowable latency)), at step 1310. In one case, if the Wi-Fi network module 646 determines that the latency of the mesh network (or wireless network) is adequate, the Wi-Fi network module 646 may send confirmation of adequate latency to the base module 638, at step 1312.

In another case, if the Wi-Fi network module 646 determines that the latency is higher (e.g., if the latency is determined to be greater than a threshold (or maximum allowable latency)), then the Wi-Fi network module 646 may send a message to the computer associated with the central hub 602 to trigger the computer to cause the one or more drones to decrease the distance between the one or more drones, at step 1314, where the message may indicate that the latency is not adequate or acceptable. In yet another case, the Wi-Fi network module 646 may send message to the central hub 602 to trigger the central hub 602 to send and add another drone in the existing mesh network (or existing wireless network), at step 1316. Network, where the message may indicate that the latency is not adequate or acceptable. For example, when the latency is 150 milliseconds, then in addition to the drones placed between Anchorage and Fairbanks, the Wi-Fi network module 646 can send signal to add another drone over the Gulf of Alaska so that the addition of another drone can help reduce the latency to 70 milliseconds. Thereafter, the Wi-Fi network module 646 may go back to step 1308 to determine the latency of the new created mesh network (or wireless network). The Wi-Fi network module 646 may continuously check the network connection (e.g., to check the latency) and modify the mesh network (or wireless network) based on the one or more network status. In one embodiment, the one or more network status may include the minimum bandwidth, maximum latency, etc.

In some embodiments, the Wi-Fi network module 646 can use the GPS coordinates of each of the drones to first determine whether the current arrangement of drones is such that the distance between the drones is at a minimum allowable distance. If the Wi-Fi network module 646 determines that the distance between two drones is greater than the minimum allowable distance, then the Wi-Fi network module 646 can send instructions to trigger one or both drones to move to minimize the distance between them as indicated at step 1314. If the Wi-Fi network module 646 determines, by analyzing of the GPS coordinates, that the drones are already at a minimum distance away from each other, then the Wi-Fi network module 646 can send instructions to trigger another drone (or other additional nodes in the mesh network, as applicable) to be deployed as indicated at step 1316.

In one embodiment, the Wi-Fi network module 646 may modify the mesh network (or wireless network) in case when the bandwidth is minimum and latency is maximum (e.g., if the Wi-Fi network module 646 determines that the bandwidth is less than a threshold value and the latency is greater than a maximum allowable latency). In another embodiment, the Wi-Fi network module 646 may send a message to a display to suspend the operation upon determining that the latency has greater than a certain percentage or multiplier of the maximum allowable latency (e.g., if the measured latency is greater than 1.2*maximum allowable latency). In yet another embodiment, the Wi-Fi network module 646 may modify the mesh network (or wireless network) in case when the latency is less than a maximum allowable latency and operation is to continue. For example, the Wi-Fi network module 646 can modify the network characteristics (e.g., latency and/or bandwidth) even if latency is not above a threshold (so that the telesurgery operation is facilitated). In such embodiments, the Wi-Fi network module 646 may reduce latency by modifying the mesh network (at more drones, and thus nodes, to the network). For example, the Wi-Fi network module 646 can send instructions to deploy an additional drone to further reduce latency in a scenario where a certain number of drones (e.g., 4 drones) can allow for latency to be below the maximum allowable latency if the Wi-Fi network module 646 determines that an additional drone is available.

In yet another embodiment, the Wi-Fi network module 646 may modify the mesh network (or wireless network) created by the one or more drones on receiving the warning range that latency increasing/bandwidth decreasing and prepare for network issues. For example, if the Wi-Fi network module 646 determines that a rate at which the latency is increasing is above a pre-determined time period is greater than a threshold value, then the Wi-Fi network module 646 can send a message to be displayed, where the message indicates that a rate at which the latency is changing is of concern. Further, the Wi-Fi network module 646 may monitor the network and send the status to the base module 638 to communicate the network status with the surgical site and remote surgeon to determine if network status may be relevant to surgical workflow (delay critical step until network speeds up). It can be noted that after the latency is determined to be adequate, the Wi-Fi network module 646 may send confirmation or a message that indicates that the latency is adequate to the base module 638, at step 1312. The Wi-Fi network module 646 may include one or more mesh router, repeaters, or the like.

Successively, the base module 638, may receive the confirmation on network connection and the modification required in drone network from the Wi-Fi network module 646, at step 822. In an exemplary embodiment, the base module 638 may receive a message that indicates that the network connection has a latency of ±70 milliseconds between the surgical site (Fairbanks) and the remote surgeon (California). Successively, the base module 638, may trigger the operation module 648 to perform the telesurgery procedure, at step 824. It can be noted that the operation of the operation module 648 is explained in FIG. 14A, FIG. 14B, and FIG. 14C.

Figure 14A:
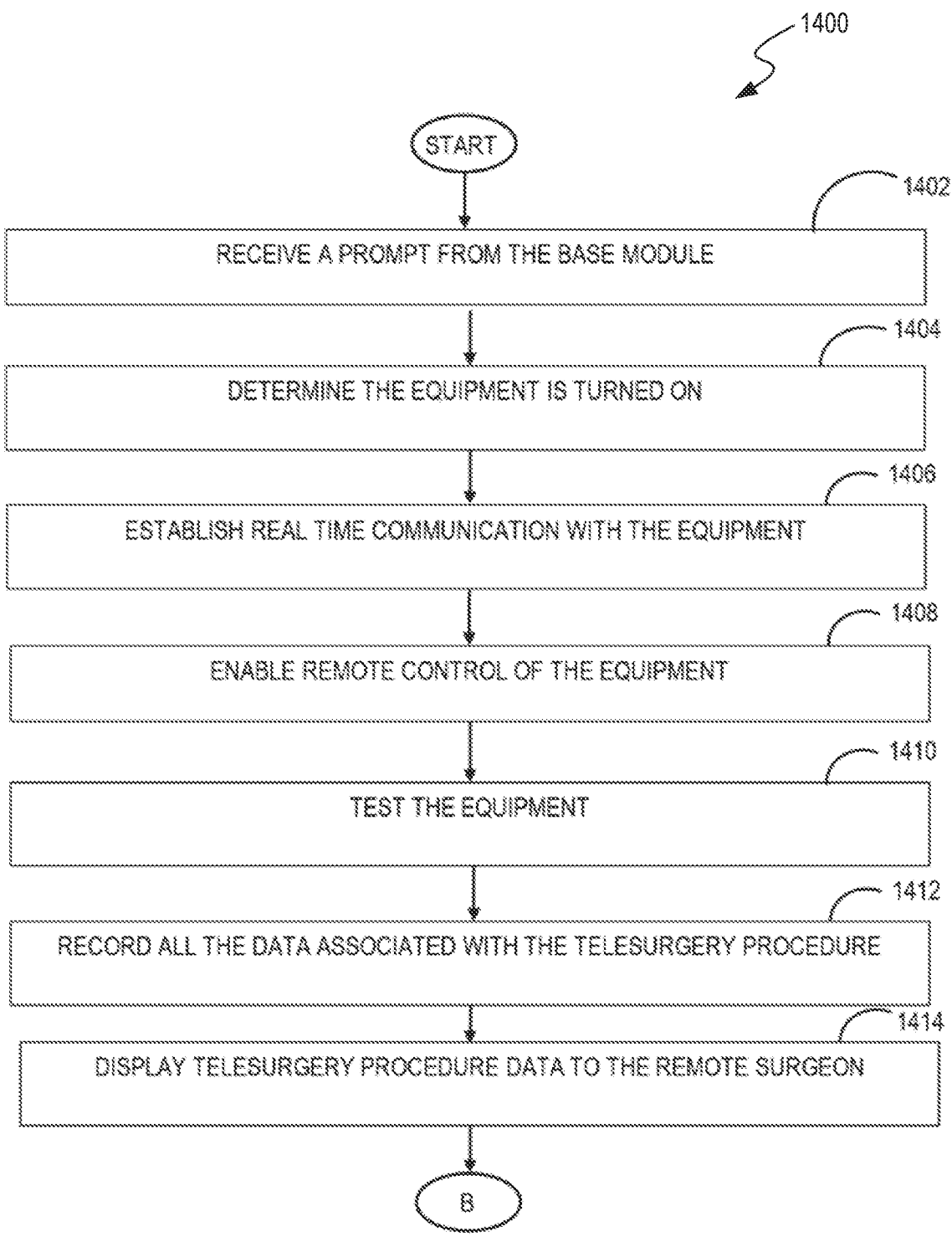
FIGS. 14A, 14B, and 14C illustrate a flow chart showing a method of operation of an operation module in the system, according to an embodiment.
Figure 14B:
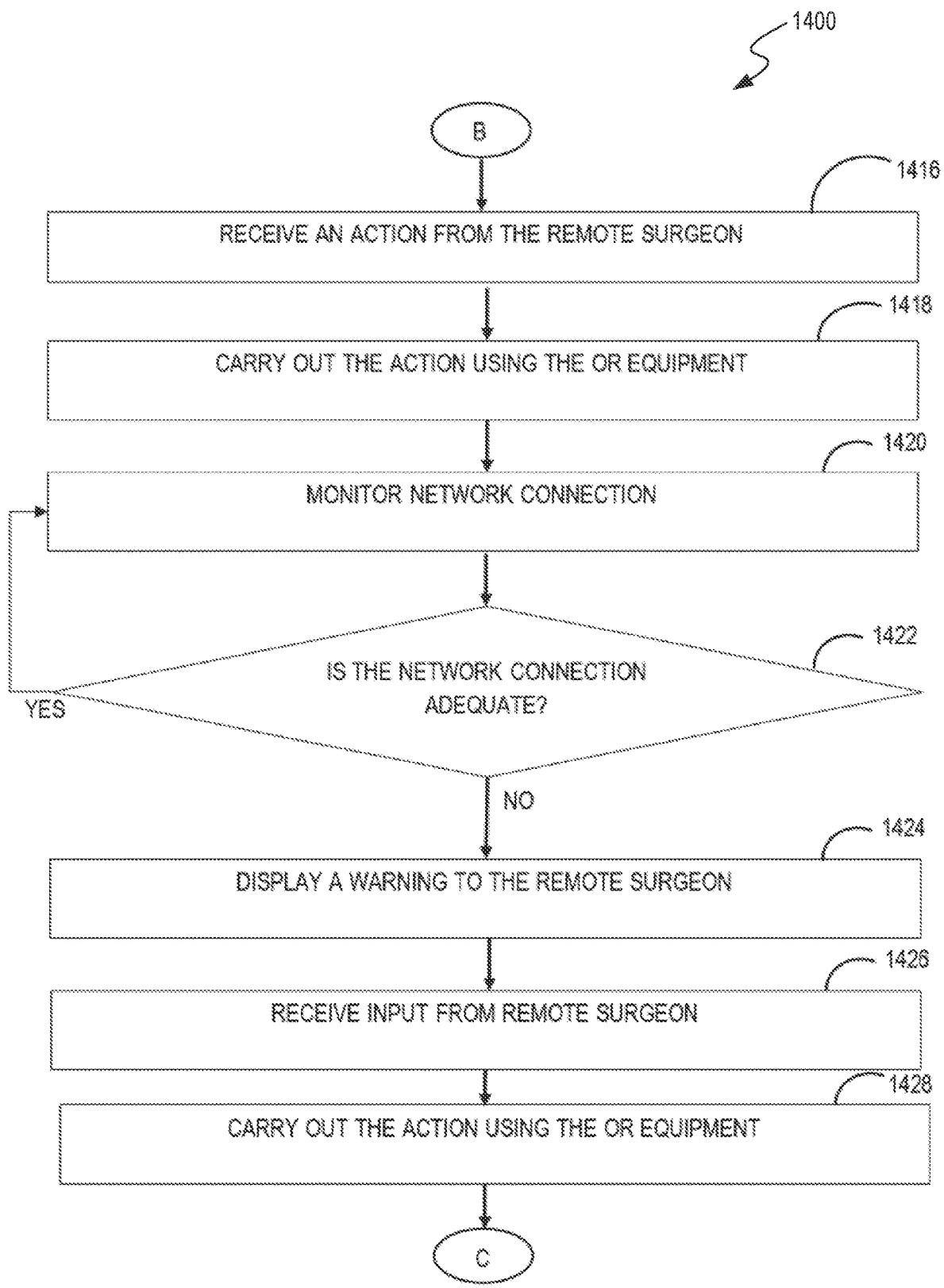
Figure 14C:
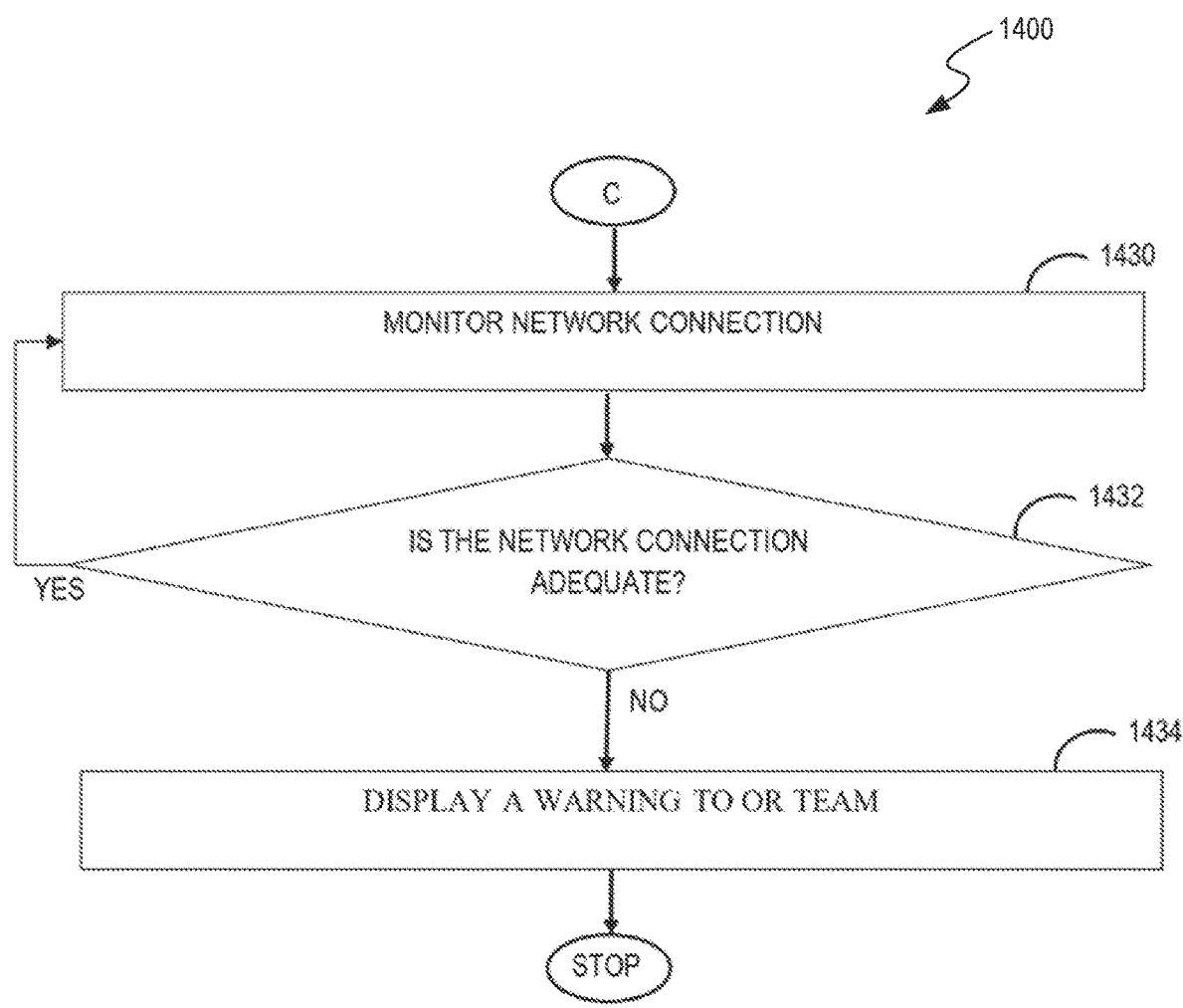

FIG. 14A, FIG. 14B, and FIG. 14C illustrate a flowchart 1400 showing a method of operation of the operation module 648, according to an embodiment. It should also be noted that in some alternative implementations, the functions noted in the blocks may occur out of the order noted in the drawings. For example, two blocks shown in succession in FIG. 14A, FIG. 14B, and FIG. 14C may be executed substantially concurrently or the blocks may sometimes be executed in the reverse order, depending upon the functionality involved. In addition, the process descriptions or blocks in flow charts should be understood as representing decisions made by a hardware structure such as a state machine. The flowchart 1400 starts at step 1402 can proceed to step 1434.

At first, the operation module 648 may receive a prompt from the base module 638, at step 1402. It can be noted that the operation module 648 may be triggered for performing the telesurgery procedure on the patient Successively, the operation module 648 may determine that the equipment is turned on, at step 1404. For example, operation module 648 determines that Ilizarov apparatus, robotic arm and end-effectors, MRI, X-RAY, and blood pressure sensors at the surgical site in Fairbanks and surgical controls 618 with the remote surgeon in California are tuned on. Further, the operation module 648 may establish the real time communication among the equipment, at step 1406. For example, the operation module 648 establishes real time communication among Ilizarov apparatus, robotic arm and end-effectors, MRI, X-RAY, and blood pressure sensors at the surgical site in Fairbanks and surgical controls 618 with the remote surgeon in California. In one embodiment, the operation module 648 may use a real time communication module to establish real time communication among the equipment. In one embodiment, the real time communication module may be used to send the audio, video, and sensors data to the remote surgeons and the surgical controls 618 to the surgical site. For example, the real time communication module may share a real time video of the telesurgery procedure with Dr. T. Further, the operation module 648 may enable a remote control of the equipment, at step 1408. For example, the operation module 648 enables Ilizarov apparatus, robotic arm and end-effectors, MRI, X-RAY, and blood pressure sensors at the surgical site in Fairbanks and surgical controls 618 with the remote surgeon in California.

Successively, the operation module 648 may test the equipment, at step 1410. In one embodiment, the operation module 648 may comprise a test equipment. Further, the test equipment may be used to check the audio and video connections and one or more sensors including, but not limited to, SpO2 sensor, temperature sensor, and heart rate sensor. Further, the test equipment may test telemetry on robotic surgical system along with data transmission, performance of robot or equipment, and ensure that all features of the equipment are operational. The test equipment may confirm the connections for audio, video, and sensors in the system 600. Further the test equipment may check telemetry on robotic surgical system for proper data transmission, performance of robotic arm and to ensure all features are working properly. Thus, the remote surgeon may then perform the telesurgery procedure. For example, Dr. T (remotely from California) perform the telesurgery on Alex in Fairbanks. Based on testing the equipment, the operation module 648 may record all data associated with the equipment and the telesurgery procedure, at step 1412. In one embodiment, data associated with the telesurgery procedure may include, but not limited to, video, audio, sensor data, robotic controls, equipment controls, network data including bandwidth and/or latency. Further, the operation module 648 may comprise an operation recording module. In one embodiment, the operation recording module may be configured to record one or more data associated with the surgery. It can be noted that the recorded one or more data associated with the surgery may be stored in the medical database 650. In one embodiment, the surgical interface may be configured to display the one or more data associated with the surgery to the remote surgeon.

Further, the operation module 648 may display the telesurgery procedure data to the remote surgeon, at step 1414. For example, the operation module 648 displays a real time video along with the real time data related to Alex, to Dr. T. In one embodiment, a remote surgeon terminal may display surgery data to the remote surgeon and enable the surgeon to send control signals to the surgical site.

Further, the operation module 648 may receive an action from the remote surgeon, at step 1416. For example, the operation module 648 receives an action from Dr. T (remotely from California) indicating that Ilizarov apparatus shall be moved around the left leg of Alex. Successively, the operation module 648 may carry out the action using an OR equipment, at the surgical site, at step 1418. For example, the operation module 648 carries out the action of moving the Ilizarov apparatus around the left leg of Alex at the surgical site in Fairbanks. Further, the operation module 648 may monitor the network connections (e.g., the latency), at step 1420. It can be noted that the network connection (e.g., latency) may be determined to be adequate by the operation module 648, at step 1422. In one case, if the operation module 648 determines that the network connection (e.g., latency) is not adequate (e.g., the operation module 648 may determine whether the latency is greater than a threshold (e.g., maximum allowable latency)), then the operation module 648 may display on a screen a warning to the remote surgeon, at step 1424. In another case, if the operation module 648 determines that the network connection is adequate (e.g., the operation module 648 may determine whether the latency is less than a threshold (e.g., maximum allowable latency)), then the operation module 648 can continue monitoring the network connection, at step 1420. Further, the operation module 648 may receive an input from the remote surgeon, at step 1426.

Further, the operation module 648 may carry out the action using the OR equipment, at step 1428. Further, the operation module 648 may monitor the network connections, at step 1430, for example, by sending a message to measure latency of the wireless network that includes one or more drones. It can be noted that the network connection may be determined to be adequate by the operation module 648, at step 1432 using the techniques described in this patent document. In one case, if the operation module 648 determines that the network connection is adequate, the operation module 648 may continue monitoring the network connection at step 1430. In another case, if the operation module 648 determines that the network connection is not adequate, then the operation module 648 may display on a screen a warning to the surgeons in the OR, at step 1434.

Successively, the base module 638, may receive the one or more data generated during the real time communication from the operation module 648, at step 826. Based on the received data, the base module 638 may finally save the data in the medical database 650, at step 828. It can be noted that the base module 638 may save the telesurgery data and the patient data to the medical database 650. For example, for performing a telesurgery procedure for a fractured leg of Alex who situated in Fairbanks, by his remote surgeon Dr. T who is situated in a telesurgery environment in California, a Ilizarov apparatus is used along with, robotic arm and end-effectors, MRI, X-RAY, and blood pressure sensors at the surgical site in Fairbanks and surgical controls 618 with the remote surgeon in California.

Figure 15:
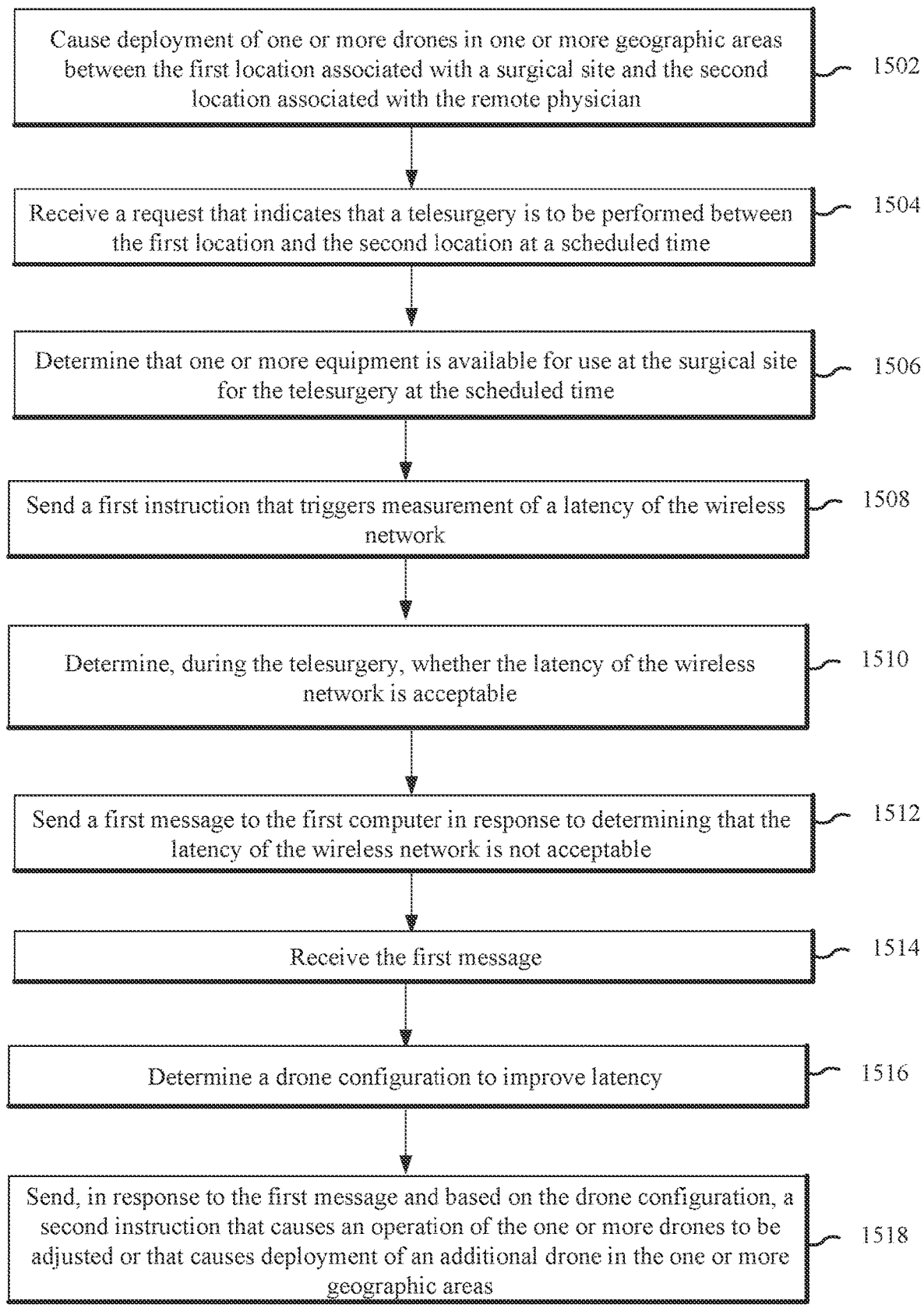
FIG. 15 is a flow diagram illustrating an example process for managing latency for a telesurgery, according to an embodiment.

FIG. 15 is a flow diagram illustrating an example process for managing latency for a telesurgery, in accordance with one or more embodiments. Operations 1502 and 1514-1518 are performed by a first computer, and operations 1504 to 1512 are performed by a second computer. Operation 1502 includes causing deployment of one or more drones in one or more geographic areas between the first location associated with a surgical site and the second location associated with the remote physician, wherein the one or more drones are operable to create a wireless network configured for communications between a device operated by the remote physician and the surgical site.

Operation 1504 includes receiving a request that indicates that a telesurgery is to be performed between the first location and the second location at a scheduled time. Operation 1506 includes determining that one or more equipment is available for use at the surgical site for the telesurgery at the scheduled time. Operation 1508 includes sending a first instruction that triggers measurement of a latency of the wireless network. Operation 1510 includes determining, during the telesurgery, whether the latency of the wireless network is acceptable. Operation 1512 includes sending a first message to the first computer in response to determining that the latency of the wireless network is not acceptable, wherein the first message indicates that the latency is not acceptable Operation 1514 includes receiving the first message. Operation 1516 includes determining a drone configuration to improve latency. A drone configuration can be determined by determining whether at least one drone can be moved from its current location to another location to improve latency, or whether to deploy another drone to a new location to improve latency, etc. Operation 1518 includes sending, in response to the first message and based on the drone configuration, a second instruction that causes an operation of the one or more drones to be adjusted or that causes deployment of an additional drone in the one or more geographic areas In some embodiments, wherein whether the latency of the wireless network is determined to be acceptable using a telesurgery management plan that includes a maximum allowable latency for the telesurgery, a plurality of surgical steps to be performed for the telesurgery, required data rate for the telesurgery, an indication of whether medical staff is available at the surgical site, and/or risk of the telesurgery on a patient. In some embodiments, the maximum allowable latency is based on at least one surgical step of the plurality of surgical steps, and/or the required data rate for the telesurgery. In some embodiments, the second processor of the second computer is further configured to: analyze a surgical plan for the telesurgery to determine data requirements for performing the telesurgery; generate a telesurgery management plan based on the data requirements, wherein the data requirements include a bandwidth required for the telesurgery; and wherein, in response to determining that the latency of the wireless network is not acceptable based on the telesurgery management plan, the second processor of the second computer is further configured to: determine, from the surgical plan, that medical staff is available at the surgical site; and cause a monitor associated with an operation room to display a second message that indicates that the latency is not acceptable and that the medical staff at the surgical site is expected to take over surgery of a patient.

In some embodiments, the second processor of the second computer is configured to determine that the latency of the wireless network is not acceptable by being configured to: determine the maximum allowable latency for performing the telesurgery from the telesurgery management plan; and determine that the latency is below the maximum allowable latency. In some embodiments, the second processor of the second computer is configured to determine that the latency of the wireless network is not acceptable by being configured to: determine that a rate at which the latency has increased within a pre-determined time window is above a pre-determined threshold. In some embodiments, the one or more drones includes a first drone and a second drone, and the second instruction indicates to the first drone to move from a first location to a second location that is closer to a location of the second drone than the first location.

In some embodiments, in response to determining that the latency of the wireless network is acceptable, the second processor of the second computer is further configured to: repeat network connection monitoring operations that include the send the first instruction to measure the latency of a wireless network and the determine, during the telesurgery, whether the latency of the wireless network is acceptable. In some embodiments, the second processor of the second computer is further configured to: receive one or more environmental factors of the one or more geographical areas, wherein the one or more environmental factors include temperature, weather, or wind; determine a second drone configuration in response to a determination that the one or more environmental factors affect the latency of the wireless network; and send, based on the second drone configuration, a third instruction that causes the operation of the one or more drones to be adjusted or that causes deployment of another drone in the one or more geographic areas.

In some embodiments, the second processor of the second computer is further configured to: schedule, in response to the receive the request, a time and determine the one or more equipment needed for the telesurgery; wherein the one or more equipment is determined to be available in response to receiving a confirmation message that indicates that the one or more equipment has arrived at the first location associated with the surgical site. In some embodiments, the wireless network includes a mesh network.

The first computer comprises a first processor and a first memory having a first set of instructions stored thereupon. The first set of instructions upon execution by the first processor configures the first processor to perform at least operations 1502 and 1514-1518, and/or the operations described for at least the central hub and the drone(s) as described in this patent document. The second computer can be communicatively coupled to the first computer (e.g., via the Internet). The second computer includes a second processor and a second memory having a second set of instructions stored thereupon. The second set of instructions upon execution by the second processor configures the second processor to perform at least operations 1504-1512 and/or the operations described for at least the base module and the modules described in FIG. 6.

In another example embodiment, a system is described for latency managed telesurgery performed between a first location associated with a surgical site and a second location associated with a remote physician. The system includes a plurality of drones and at least one computer. The plurality of drones configured to wirelessly communicate with each other to provide a mesh network. The at least one computer programmed to: analyze a surgical plan to determine telesurgery data requirements for a telesurgery procedure; and generate a drone control plan based on the telesurgery data requirements and communication capabilities of the plurality of drones, wherein the drone control plan is configured to maintain the mesh network for one or more surgical steps of the telesurgery procedure.

In some embodiments, analyzing the surgical plan includes: determining data requirements for surgical equipment at the first location to be used according to the robotic surgical plan; determining at least one safety factor for the one or more surgical steps; and determining the telesurgery data requirements based on the data requirements for concurrently used surgical equipment and the associated at least one safety factor. In some embodiments, the determine telesurgery data requirements includes a minimum data rate of the mesh network for completing the one or more surgical steps. In some embodiments, the drone control plan is further based on telesurgery data requirements of one or more additional telesurgery procedure to be performed concurrently with the one or more surgical steps of the telesurgery procedure. In some embodiments, the drone control plan includes any one or more of: positioning of the plurality of drones, one or more communication channels for the mesh network, power consumption plan for at least one of the drones; throttling bandwidth; and communication protocols.

In some embodiments, the at least one computer is further configured to manage resources of the plurality of drones by determining an availability of resources to be allocated to facilitate execution of telesurgery communications for the telesurgery procedure. In some embodiments, the at least one computer is further configured to: determine an amount of resources of the system for telesurgery actions to execute; and implement one or more corrective measures to free up the amount of the resources. In some embodiments, the resources include CPU capacity, memory, and/or communication bandwidth. In some embodiments, the at least one computer is further configured to: simulate the telesurgery procedure using available surgical equipment according to the surgical plan to determine telesurgery data requirements. In some embodiments, the at least one computer is further configured to: prioritize communications for the one or more surgical steps based on at least one priority level of the one or more steps. In some embodiments, the at least one computer is further configured to: determine a latency setting for one or more surgical steps; and control the plurality of drones based on the determined latency setting.

III. Techniques and/or Devices to Perform Telesurgery

The wireless network in which a set of drones (e.g., one or more drones) operate can be an adaptive wireless network so that the operation of the set of drones (or additional drones) can change the wireless communication characteristics of the wireless network. For example, as explained in this patent document, an addition of a drone can help reduce latency if two drones are far apart from each other. In another example, the base module described in this patent document can determine the best route for transmitting signal from a source via two or more drones (which may be in a mesh network) to a destination (e.g., the computer or data system 450).

The base module can perform the following upon receiving a request to schedule a telesurgery (e.g., as shown in step 802 in FIG. 8): (1) determine equipment needed to perform the telesurgery (e.g., as shown in step 812 of FIG. 8 and in FIG. 12), and (2) determine a telesurgery management plan.

The telesurgery management plan may include a maximum allowable latency, a surgical plan (e.g., steps to be performed before/during a telesurgery), surgery apparatus requirement (e.g., a list of equipment needed for the surgery), risk to the patient (e.g., a number from 0 to 1 that identifies a risk to patient if wireless network, where 0 is no risk and 1 is significant risk); data rates needed for the surgery, and availability of medical staff at the surgical site where the patient is being operated.

In some embodiments, the base module can include a maximum allowable latency in a telesurgery management plan, where the maximum allowable latency is received from the equipment setup module 642, and where the maximum allowable latency may be based at least on type of equipment and/or surgical locations as explained in this patent document. In some embodiments, the maximum allowable latency may be determined based on the type of equipment used for performing the telesurgery. For example, if the equipment requires an audio and a video data transmission, the maximum allowable latency may be higher than the maximum allowable latency for an equipment that only requires video data transmission. in another example, the telesurgery management plan may include data rate needed for the surgery to facilitate audio and/or video data transmission, where the maximum allowable latency may be based on the data rate needed or the data requirements for the surgery.

The telesurgery management plan may also include a list of steps (e.g., included in a surgical plan) to be performed during the telesurgery for a successful surgery and an indication that a local medical staff is located where the patent is being operated. In some embodiments, list of steps may identify steps that can be performed by a remote surgeon (away from the patient on whom the surgery is performed) and/or steps performed by local medical staff or local surgeon located close to or in same location as the patient. For example, during a particular step that can be performed remotely and by local medical staff or local surgeon, if the base module determines that during the measured latency during that step is greater than the maximum allowable latency, and if the base module determines that local medical staff is available to take over the surgery, then the base station can send a message to be displayed on a monitor to indicate to the local medical staff or local surgeon to take over the surgery.

In this patent document, the module/modules that determine to add a drone to an existing set of drone or change one or more positions of the one or more deployed drones can do so based on a drone configuration. The drone configuration may include a list of drones deployed, their current position, type of network formed by the deployed drone (e.g., mesh network), and latest measured latency. For example, based on the latest measured latency and the current positions of two drones, the base module can determine to add another drone to the wireless network to improve latency or can send instruction(s) to move one or both drones to improve latency.

In some embodiments, the telesurgery management plan can be changed. For example, the maximum allowable latency can be increased or decreased manually via a user interface. The base module can display the telesurgery management plan so that a user can, via the user interface, change the telesurgery management plan (e.g., changing the maximum allowable latency, or changing the indication of whether medical staff is available locally at the surgical site where the patient will be operated on).

In some embodiments, a system for low latency telesurgery may include a central hub and a base module. The central hub includes one or more drones to create a mesh network in one or more geographic areas between a surgical site and a remote surgeon. The base module may be communicatively coupled to the central hub via a cloud network. The base module can be configured to: (1) schedule a time and determine one or more equipment for the telesurgery between the remote surgeon and the surgical site; (2) test latency of the mesh network for performing the telesurgery at the scheduled time and with determined one or more equipment; (3) determine available equipment among the one or more equipment at the scheduled time; (4) monitor the availability of equipment and latency of the mesh network during the telesurgery; and based on the available equipment, perform the telesurgery at the surgical site, by the remote surgeon.

Regarding (2) mentioned above, the latency can be tested by simulating surgical procedure (e.g., imaging, robot control data, voice data, diagnostic data, etc.), generating telesurgery management plan based on available equipment, developing testing plan based on available equipment, etc. Regarding (4) mentioned above, the availability of the equipment can be monitored by prioritizing equipment and throttle non-critical equipment; select and schedule equipment based on network and modified network. Regarding (5) mentioned above, the telesurgery is performed by using the telesurgery management plan for managing latency and/or adjusting the telesurgery management plan based on changed to planned latency, etc.

Figure 16:
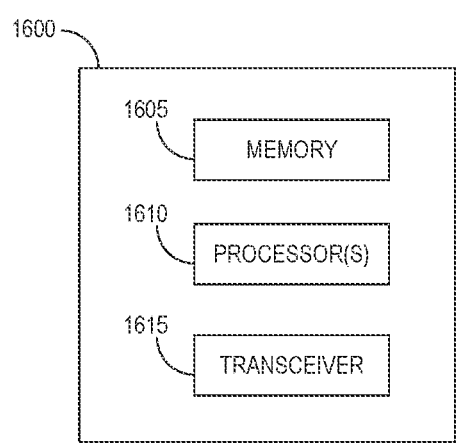
FIG. 16 shows an exemplary block diagram of a computer for performing a latency managed telesurgery, according to an embodiment.

FIG. 16 shows an exemplary block diagram of a computer 1600 (e.g., first computer or second computer) for performing a latency managed telesurgery. The computer 1600 may include one or more servers, where each server may be configured to perform operations associated with one or more modules as described in this patent document. The first computer may be associated with the central hub (shown as 602 in FIG. 6) and may include a module that can receive instructions from the second computer and/or send instructions to deploy/adjust operation of one or more drones. The second computer may include a base module and/or one or more modules described in FIG. 6. The computer 1600 includes at least one processor 1610 and a memory 1605 having instructions stored thereupon. The instructions upon execution by the processor 1610 configure the computer 1600 to perform the operations described in FIGS. 1 to 15 and in the various embodiments described in this patent document. The transceiver 1615 transmits information to and/or receives information from another device (e.g., another computer/server).

Advanced surgical systems include many different types of equipment to monitor and anesthetize the patient, assist the surgeon in performing surgical tasks, and maintain the environment of the operating room. Non-limiting examples of surgical equipment that may be used or improved by the present invention are provided for reference.

Vital signs monitor refers to medical diagnostic instruments and in particular to a portable, battery powered, multi-parametric, vital signs monitoring device that can be used for both ambulatory and transport applications as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station. A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into the embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into the embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into the embodiments in a variety of manners.

End Tidal CO2 monitor or capnography monitor refers to an instrument which is used for measurement of level of carbon dioxide (referred to as end tidal carbon dioxide, ETCO2) that is released at the end of an exhaled breath. End Tidal CO2 monitor or capnography monitor is widely used in anesthesia and intensive care. ETCO2 can be calculated by plotting expiratory CO2 with time. Further, ETCO2 monitor plays a very crucial role for the measurement of applications such as Cardiopulmonary Resuscitation (CPR), Airway assessment, Procedural sedation and analgesia, pulmonary diseases such as obstructive pulmonary disease, pulmonary embolism, etc., heart failure, metabolic disorders, etc. The instrument can be configured as side stream (diverting) or mainstream (non-diverting). Diverting device transports, a portion of a patient's respired gases from the sampling site to the sensor while non-diverting device does not transport gas away. Also, measurement by the instrument is based on the absorption of infrared light by carbon dioxide; where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into the embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be: auscultatory or oscillometric. A blood pressure monitor can be integrated into the embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into the embodiments in a variety of manners.

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into the embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, cardiomyopathy. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into the embodiments in a variety of manners.

Neuromonitoring also called Intraoperative neurophysiological monitoring (abbreviated as IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), Somatosensory Evoked Potential (SSEP), transcranial electrical motor evoked potentials (TCeMEP), Electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into the embodiments in a variety of manners.

Motor Evoked Potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into the embodiments in a variety of manners.

Somatosensory evoked potential abbreviated as SSEP, or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. Somatosensory evoked potential can be integrated into the embodiments in a variety of manners.

Electromyography abbreviated as EMG refers to the evaluation and recording of electrical signals or electrical activity of the skeletal muscles. Electromyography instrument or Electromyograph or Electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into the embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are Alpha, Beta, Theta, and Delta. Electroencephalography can be integrated into the embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into the embodiments in a variety of manners.

A microscope refers to an instrument that is used for viewing samples & objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), Scanning Electron abbreviated as SEM (electron illuminated and image seen with the microscope in black and white), Transmission Electron Microscope abbreviated as TEM (electron illuminated and image seen with the microscope is the high magnification and high resolution). A microscope can be integrated into the embodiments in a variety of manners.

Endoscopes or arthroscopes or laparoscopes refer to minimally invasive surgical techniques where procedures are performed by performing minimal incision in the body. An Endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, etc. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. Endoscopes/arthroscopes/laparoscopes or minimally invasive surgery techniques can be integrated into the embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors comprise a light source, optical fiber, external transducer, and photodetector. Fiber-optic sensors may be intrinsic or extrinsic. Fiber optics sensors may be categorized into four types physical, imaging, chemical, and biological. Fiber optics can be integrated into the embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into the embodiments in a variety of manners.

High definition monitors refer to a display in which a clearer picture than possible with low-definition, low-resolution screens. High-definition monitors have a higher density of pixels per inch than past standard TV screens. Resolution for high definition monitors may be 1280×720 pixels or more. Full HD—1920×1080, Quad HD-2560×1440, 4K-3840×2160, 8K-7680×4320 pixels. High definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), better visualization of blood vessels and lesions. High definition monitors can be integrated into the embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. Operating room cameras can be integrated into the embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, sensors, etc. A surgical tower can be integrated into the embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. Electrocautery can be integrated into the embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. Radiofrequency can be integrated into the embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. Laser can be integrated into the embodiments in a variety of manners.

Sensors are used in association with minimally invasive surgery devices. The sensor may be used in minimally invasive surgeries for tactile sensing of tool—tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into the embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, Fluoroscopy, Magnetic resonance imaging (MRI), Ultrasound, Endoscopy, Elastography, Tactile imaging, Thermography, Medical photography, and nuclear medicine e.g., Positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. Imaging systems can be integrated into the embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, etc. An X-ray can be integrated into the embodiments in a variety of manners.

Magnetic resonance imaging abbreviated as MRI refers to a medical imaging instrument that uses powerful magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release is dependent on environmental factors and the chemical nature of the molecules. MRI may more widely suit for imaging of non-bony parts or soft tissues of the body. MRI may be less harmful as it does not use damaging ionizing radiation as in the X-ray instrument. MRI instrument may consist of magnets, gradients, radiofrequency system, computer control system. Some areas where imaging by MRI should be prohibited may be people with implants. MRI can be integrated into the embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of x-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. CT can be integrated into the embodiments in a variety of manners.

Stereotactic navigation systems refer to an instrument that uses patient imaging (e.g., CT, MRI) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into the embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, etc., in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. Ultrasound can be integrated into the embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into the embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. Surgical bed can be integrated into the embodiments in a variety of manners.

Disposable air warmer (also referred to as bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into the embodiments in a variety of manners.

Sequential compression device abbreviated as SVD refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into the embodiments in a variety of manners.

Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into the embodiments in a variety of manners.

Bed position controller refers to an instrument for controlling the position of the patient bed. Positioning a patient in bed is important for maintaining alignment and for preventing bed-sores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. Bed position controller can be integrated into the embodiments in a variety of manners.

Operating room environmental controls refers to control or maintenance of the environment in an operation theatre where procedures are performed to minimize the risk of airborne infection and provide a conducive environment for everyone in the operation theatre—surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. Operating room environmental controls can be integrated into the embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into the embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or High-Efficiency Particulate Air filter. High-Efficiency Particulate Air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into the embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into the embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. Drill can be integrated into the embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. Scalpel can be integrated into the embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. Stitches can be integrated into the embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium, and they are thicker, stronger, and larger. The stapler can be integrated into the embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into the embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components gas delivery system, power source, control system, safety feature, gas filter, monitor. A ventilator can be integrated into the embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. Continuous positive airway pressure instruments can be integrated into the embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are time-saving, no risk of healthcare-associated infections, cost-efficient) or sterilizable (cross-contamination, risk of surgical site infections, sterilization). Consumables can be integrated into the embodiments in a variety of manners.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into Surgical Robotic Systems, Rehabilitative Robotic Systems, Non-invasive Radiosurgery Robots, Hospital & Pharmacy Robotic Systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally-invasive procedures. The systems comprise computer-controlled electromechanical devices that work in response to controls manipulated by the surgeons. Robotic systems can be integrated into the embodiments in a variety of manners.

An Electronic Health Record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into the embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including Radio-frequency Identification (RFID), Global Positioning System (GPS), Bluetooth Low Energy (BLE), barcodes, Near-Field Communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into the embodiments in a variety of manners.

Quantum computing refers to any computational device or method which utilizes properties of quantum states defined by quantum mechanics such as superposition, entanglement, etc. to perform computations. These devices utilize qubits which are the quantum equivalent to bits in a classical computing system, comprised of at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

What is claimed is:

1. A system for latency managed telesurgery performed between a first location associated with a surgical site and a second location associated with a remote physician, the system comprising:
   a first computer comprising a first processor and a first memory having a first set of instructions stored thereupon, the first set of instructions upon execution by the first processor configures the first processor to:
      cause deployment of one or more drones in one or more geographic areas between the first location associated with a surgical site and the second location associated with the remote physician, wherein the one or more drones are operable to create a wireless network configured for communications between a device operated by the remote physician and the surgical site;
   a second computer communicatively coupled to the first computer, the second computer includes a second processor and a second memory having a second set of instructions stored thereupon, the second set of instructions upon execution by the second processor configures the second processor to:
      receive a request that indicates that a telesurgery is to be performed between the first location and the second location at a scheduled time;
      determine that one or more equipment is available for use at the surgical site for the telesurgery at the scheduled time;
      send a first instruction that triggers measurement of a latency of the wireless network;
      determine, during the telesurgery, whether the latency of the wireless network is acceptable; and
      send a first message to the first computer in response to determining that the latency of the wireless network is not acceptable, wherein the first message indicates that the latency is not acceptable; and
   the first computer comprising the first processor is further configured to:
      receive the first message;
      determine a drone configuration to improve latency; and
      send, in response to the first message and based on the drone configuration, a second instruction that causes an operation of the one or more drones to be adjusted or that causes deployment of an additional drone in the one or more geographic areas.

2. The system of claim 1, wherein whether the latency of the wireless network is determined to be acceptable using a telesurgery management plan that includes a maximum allowable latency for the telesurgery, a plurality of surgical steps to be performed for the telesurgery, required data rate for the telesurgery, an indication of whether medical staff is available at the surgical site, and/or risk of the telesurgery on a patient.

3. The method of claim 2, wherein the maximum allowable latency is based on at least one surgical step of the plurality of surgical steps, and/or the required data rate for the telesurgery.

4. The system of claim 1,
   wherein the second processor of the second computer is further configured to:
      analyze a surgical plan for the telesurgery to determine data requirements for performing the telesurgery;
      generate a telesurgery management plan based on the data requirements, wherein the data requirements include a bandwidth required for the telesurgery; and
   wherein, in response to determining that the latency of the wireless network is not acceptable based on the telesurgery management plan, the second processor of the second computer is further configured to:
      determine, from the surgical plan, that medical staff is available at the surgical site; and
      cause a monitor associated with an operation room to display a second message that indicates that the latency is not acceptable and that the medical staff at the surgical site is expected to take over surgery of a patient.

5. The system of claim 1, wherein the second processor of the second computer is configured to determine that the latency of the wireless network is not acceptable by being configured to:
   determine the maximum allowable latency for performing the telesurgery from the telesurgery management plan; and
   determine that the latency is below the maximum allowable latency.

6. The system of claim 1, wherein the second processor of the second computer is configured to determine that the latency of the wireless network is not acceptable by being configured to:
   determine that a rate at which the latency has increased within a pre-determined time window is above a pre-determined threshold.

7. The system of claim 1,
   wherein the one or more drones includes a first drone and a second drone, and
   wherein the second instruction indicates to the first drone to move from a first location to a second location that is closer to a location of the second drone than the first location.

8. The system of claim 1, wherein in response to determining that the latency of the wireless network is acceptable, the second processor of the second computer is further configured to:
   repeat network connection monitoring operations that include the send the first instruction to measure the latency of a wireless network and the determine, during the telesurgery, whether the latency of the wireless network is acceptable.

9. The system of claim 1, wherein the second processor of the second computer is further configured to:
   receive one or more environmental factors of the one or more geographical areas, wherein the one or more environmental factors include temperature, weather, or wind;
   determine a second drone configuration in response to a determination that the one or more environmental factors affect the latency of the wireless network; and
   send, based on the second drone configuration, a third instruction that causes the operation of the one or more drones to be adjusted or that causes deployment of another drone in the one or more geographic areas.

10. The system of claim 1, wherein the second processor of the second computer is further configured to:
    schedule, in response to the receive the request, a time and determine the one or more equipment needed for the telesurgery;
    wherein the one or more equipment is determined to be available in response to receiving a confirmation message that indicates that the one or more equipment has arrived at the first location associated with the surgical site.

11. The system of claim 1, wherein the wireless network includes a mesh network.

12. A method comprising:
- receiving, by a computer, a request that indicates that a telesurgery is to be performed between a first location and a second location at a scheduled time, wherein the first location is associated with a surgical site and the second location is associated with a remote physician;
- determining that one or more equipment is available for use at the surgical site for the telesurgery at the scheduled time;
- sending a first instruction that triggers measurement of a latency of a wireless network, wherein the wireless network includes one or more drones deployed in one or more geographic areas between the first location and the second location;
- determining, during the telesurgery, whether the latency of the wireless network is acceptable; and
- sending a first message to the first computer in response to determining that the latency of the wireless network is not acceptable, wherein the first message indicates that the latency is not acceptable, and wherein an operation of the one or more drones is adjusted or an additional drone is deployed in the one or more geographic areas.

13. The method of claim 12, whether the latency of the wireless network is determined to be acceptable using a telesurgery management plan that includes a maximum allowable latency for the telesurgery, a plurality of surgical steps to be performed for the telesurgery, required data rate for the telesurgery, an indication of whether medical staff is available at the surgical site, and/or risk of the telesurgery on a patient.

14. The method of claim 12, wherein the maximum allowable latency is based on at least one surgical step of the plurality of surgical steps, and/or the required data rate for the telesurgery.

15. The method of claim 12, further comprising:
- analyzing a surgical plan for the telesurgery to determine data requirements for performing the telesurgery;
- generating a telesurgery management plan based on the data requirements, wherein the data requirements include a bandwidth required for the telesurgery; and
- in response to determining that the latency of the wireless network is not acceptable based on the telesurgery management plan, the method further includes:
  - determining, from the surgical plan, that medical staff is available at the surgical site; and
  - causing a monitor associated with an operation room to display a second message that indicates that the latency is not acceptable and that the medical staff at the surgical site is expected to take over surgery of a patient.

16. A non-transitory computer-readable storage medium storing computer instructions, which when executed by one or more computer processors, cause the one or more computer processors to perform a method, comprising:
- receiving, by a computer, a request that indicates that a telesurgery is to be performed between a first location and a second location at a scheduled time, wherein the first location is associated with a surgical site and the second location is associated with a remote physician;
- determining that one or more equipment is available for use at the surgical site for the telesurgery at the scheduled time;
- sending a first instruction that triggers measurement of a latency of a wireless network, wherein the wireless network includes one or more drones deployed in one or more geographic areas between the first location and the second location;
- determining, during the telesurgery, whether the latency of the wireless network is acceptable; and
- sending a first message to the first computer in response to determining that the latency of the wireless network is not acceptable, wherein the first message indicates that the latency is not acceptable, and wherein an operation of the one or more drones is adjusted or an additional drone is deployed in the one or more geographic areas.

17. The non-transitory computer-readable storage medium of claim 16, whether the latency of the wireless network is determined to be acceptable using a telesurgery management plan that includes a maximum allowable latency for the telesurgery, a plurality of surgical steps to be performed for the telesurgery, required data rate for the telesurgery, an indication of whether medical staff is available at the surgical site, and/or risk of the telesurgery on a patient.

18. The non-transitory computer-readable storage medium of claim 17, wherein the latency of the wireless network is determined not to be acceptable by:
- determining the maximum allowable latency for performing the telesurgery from the telesurgery management plan; and
- determining that the latency is below the maximum allowable latency.

19. The non-transitory computer-readable storage medium of claim 16, wherein the latency of the wireless network is determined not to be acceptable by:
- determining that a rate at which the latency has increased within a pre-determined time window is above a pre-determined threshold.

20. The non-transitory computer-readable storage medium of claim 16, further comprising:
- scheduling, in response to the receive the request, a time and determine the one or more equipment needed for the telesurgery;
- wherein the one or more equipment is determined to be available in response to receiving a confirmation message that indicates that the one or more equipment has arrived at the first location associated with the surgical site.

* * * * *